(12) United States Patent
Lee et al.

(10) Patent No.: US 9,919,238 B2
(45) Date of Patent: Mar. 20, 2018

(54) DISTILLATION APPARATUS

(71) Applicant: LG CHEM, LTD., Seoul (KR)

(72) Inventors: Sung Kyu Lee, Daejeon (KR); Joon Ho Shin, Daejeon (KR); Sung Kyun Kim, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/905,618

(22) PCT Filed: Jul. 18, 2014

(86) PCT No.: PCT/KR2014/006573
§ 371 (c)(1),
(2) Date: Jan. 15, 2016

(87) PCT Pub. No.: WO2015/009116
PCT Pub. Date: Jan. 22, 2015

(65) Prior Publication Data
US 2016/0193541 A1 Jul. 7, 2016

(30) Foreign Application Priority Data

Jul. 18, 2013 (KR) .................. 10-2013-0084495
Jul. 18, 2013 (KR) .................. 10-2013-0084496
(Continued)

(51) Int. Cl.
*B01D 3/14* (2006.01)
*C07C 67/54* (2006.01)
(Continued)

(52) U.S. Cl.
CPC ............. *B01D 3/141* (2013.01); *B01D 3/008* (2013.01); *B01D 3/143* (2013.01); *B01D 3/32* (2013.01);
(Continued)

(58) Field of Classification Search
CPC .......... B01D 3/14; B01D 3/141; B01D 3/143; B01D 3/008; B01D 3/36; B01D 3/40;
(Continued)

(56) References Cited

U.S. PATENT DOCUMENTS 2,081,601 A * 5/1937 Ridgway ............. B01D 3/4261
196/132
2,108,659 A * 2/1938 Dunham ................ B01D 3/143
196/139
(Continued)

FOREIGN PATENT DOCUMENTS

CN 1227132 A 9/1999
CN 1759096 A 4/2006
(Continued)

Primary Examiner — Jonathan Miller
Assistant Examiner — Jonathan Luke Pilcher
(74) Attorney, Agent, or Firm — Dentons US LLP

(57) ABSTRACT

The present application relates to a distillation apparatus and a separation method, and according to the distillation apparatus and the separation method of the present application, it is possible to separate a material to be separated during the separation of a mixture of three or more components, for example, 2-ethylhexyl acrylate with high purity, and to achieve an object of saving energy during the separation and purification process of 2-ethylhexyl acrylate.

16 Claims, 8 Drawing Sheets

(30) Foreign Application Priority Data

Sep. 5, 2013 (KR) ........................ 10-2013-0106471
Jul. 18, 2014 (KR) ........................ 10-2014-0091326

(51) Int. Cl.
| | |
|---|---|
| *C07C 41/42* | (2006.01) |
| *C07C 69/54* | (2006.01) |
| *B01D 3/00* | (2006.01) |
| *B01D 3/32* | (2006.01) |

(52) U.S. Cl.
CPC ................ *C07C 67/54* (2013.01); *B01D 3/14* (2013.01); *C07C 41/42* (2013.01); *C07C 69/54* (2013.01)

(58) Field of Classification Search
CPC ........ B01D 1/007; B01D 3/32; B01D 3/4261; B01D 3/322; B01D 3/20; B01D 3/4283; C07C 41/42; C07C 67/54; C07C 69/54
USPC .......................................................... 203/84
See application file for complete search history.

(56) References Cited

U.S. PATENT DOCUMENTS

| | | | | |
|---|---|---|---|---|
| 2,763,604 | A * | 9/1956 | Dorsey | C07C 7/08 203/60 |
| 4,559,108 | A * | 12/1985 | Ahlberg | B01D 1/2806 202/154 |
| 5,211,817 | A * | 5/1993 | Adams | B01D 3/143 203/82 |
| 6,294,056 | B1 * | 9/2001 | Matsumoto | B01D 3/008 202/158 |
| 7,462,277 | B2 * | 12/2008 | Adrian | B01D 3/141 208/115 |
| 8,888,076 | B2 | 11/2014 | Tamminen et al. | |
| 2004/0000470 | A1 | 1/2004 | Gentilcore | |
| 2005/0038282 | A1 | 2/2005 | Sugise et al. | |
| 2006/0005574 | A1 * | 1/2006 | Glatthaar | B01D 3/141 62/643 |
| 2011/0172458 | A1 | 7/2011 | Merenov et al. | |
| 2016/0158667 | A1 * | 6/2016 | Lee | B01D 3/008 203/98 |
| 2016/0193540 | A1 * | 7/2016 | Lee | B01D 3/008 203/22 |

FOREIGN PATENT DOCUMENTS

| | | |
|---|---|---|
| CN | 101607908 A | 12/2009 |
| CN | 101798528 A | 8/2010 |
| EP | 1680393 B1 | 10/2004 |
| EP | 1280787 B1 | 1/2008 |
| EP | 2659943 A2 | 11/2013 |
| JP | 52-62958 A | 5/1977 |
| JP | 56-113717 A | 9/1981 |
| JP | 5-78267 U | 10/1993 |
| JP | 10-57704 A | 3/1998 |
| JP | 11-347301 A | 12/1999 |
| JP | 2003-532720 A | 11/2003 |
| JP | 2005-230583 A | 9/2005 |
| JP | 2006-036659 A | 2/2006 |
| JP | 2013-525097 A | 6/2013 |
| KR | 10-2012-0076193 A | 7/2012 |
| WO | 97-29068 A1 | 8/1997 |
| WO | 2005/037769 A1 | 4/2005 |
| WO | 2012/091397 A2 | 7/2012 |

* cited by examiner

[Fig. 1]
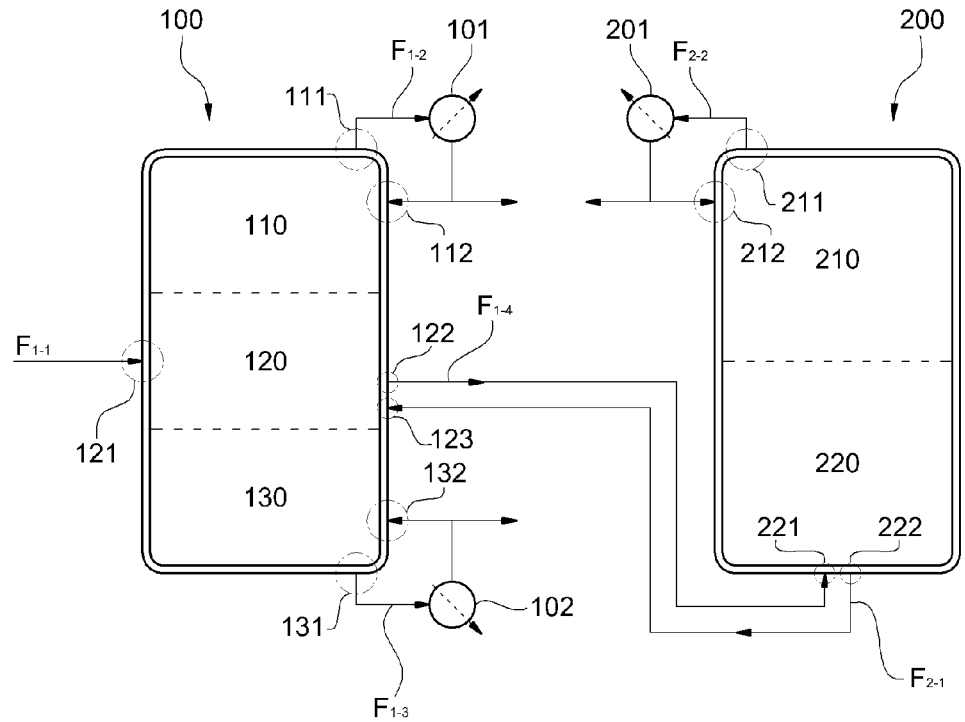
[Fig. 2]
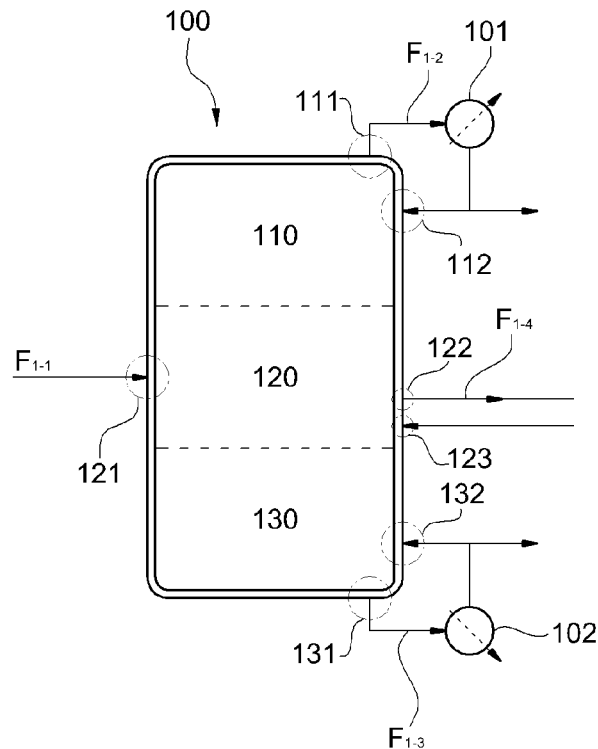

[Fig. 3]
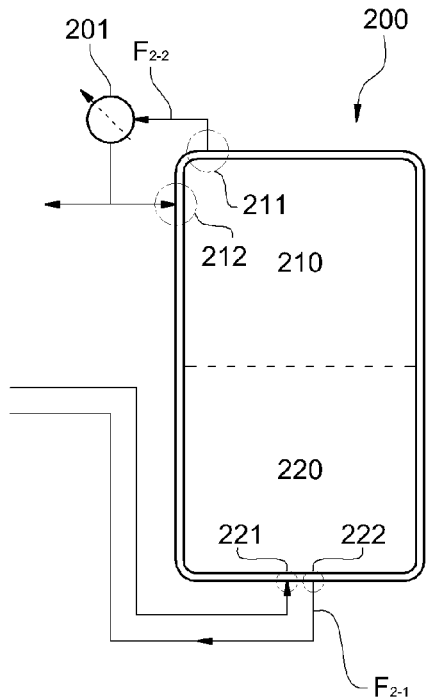
[Fig. 4]
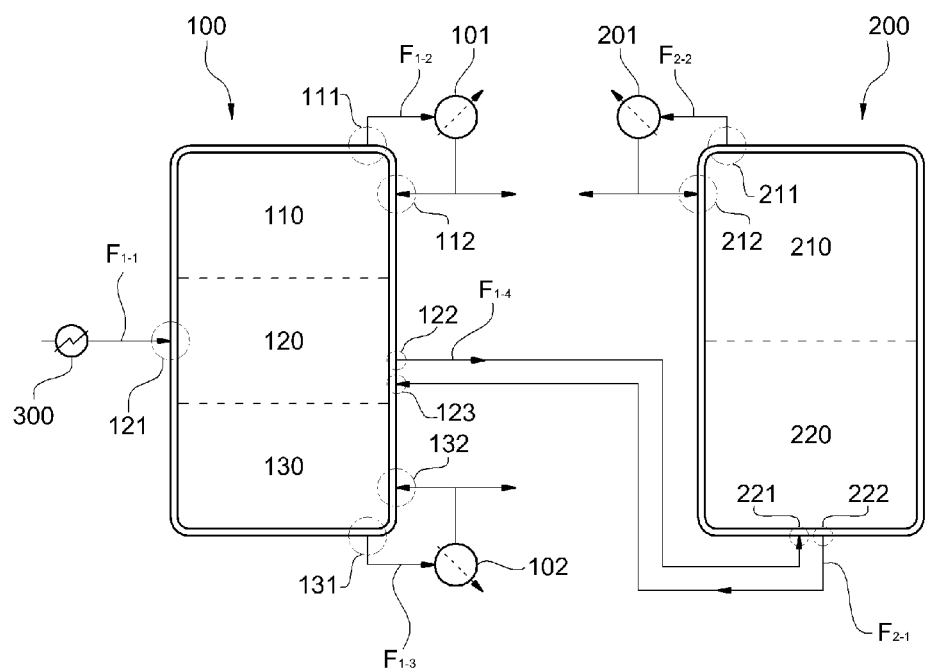

[Fig. 5]
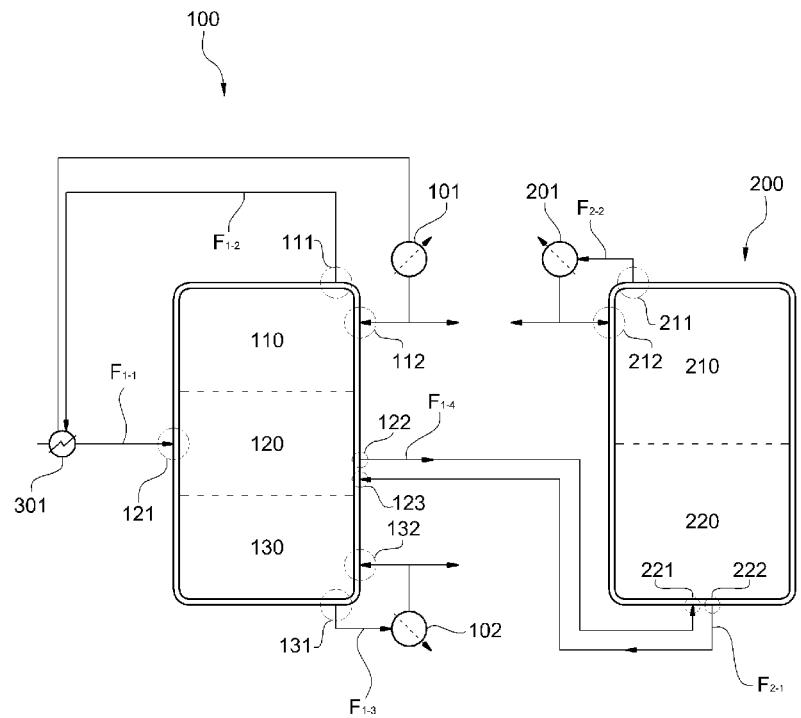
[Fig. 6]
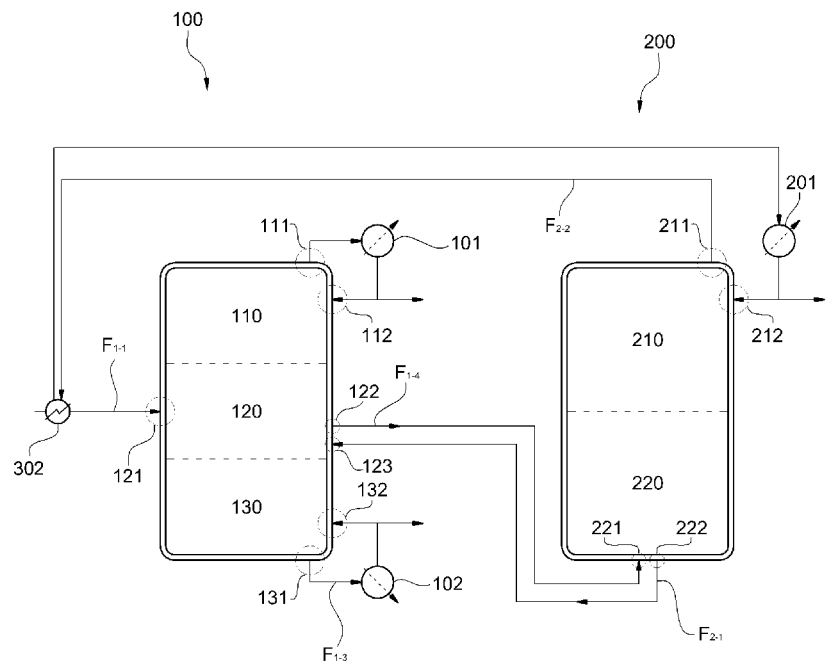

[Fig. 7]
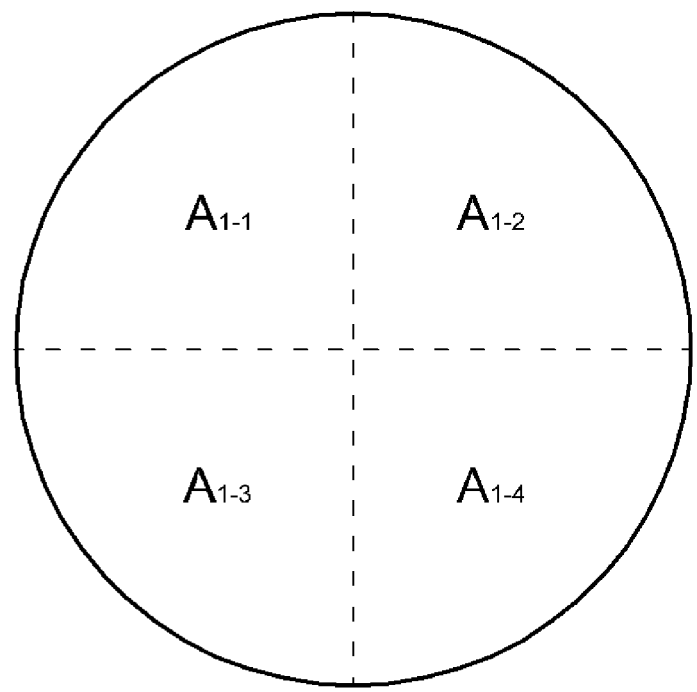
[Fig. 8]
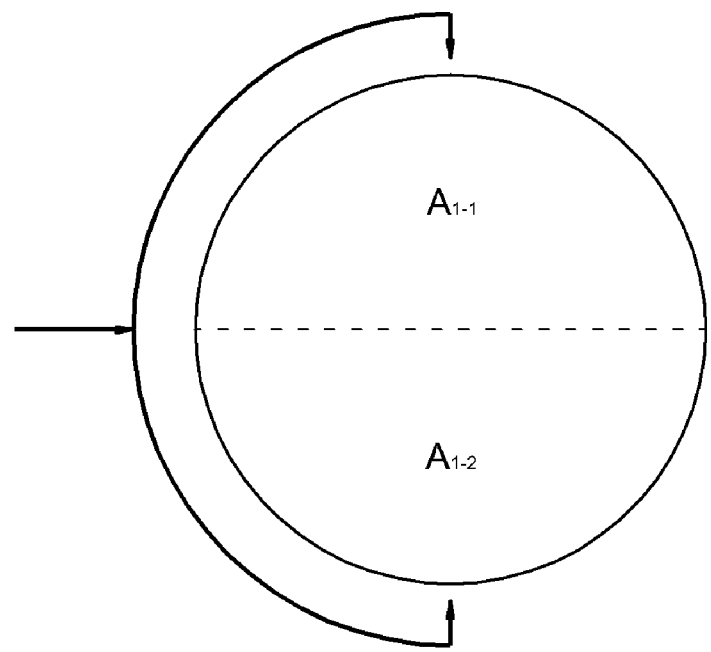

[Fig. 9]
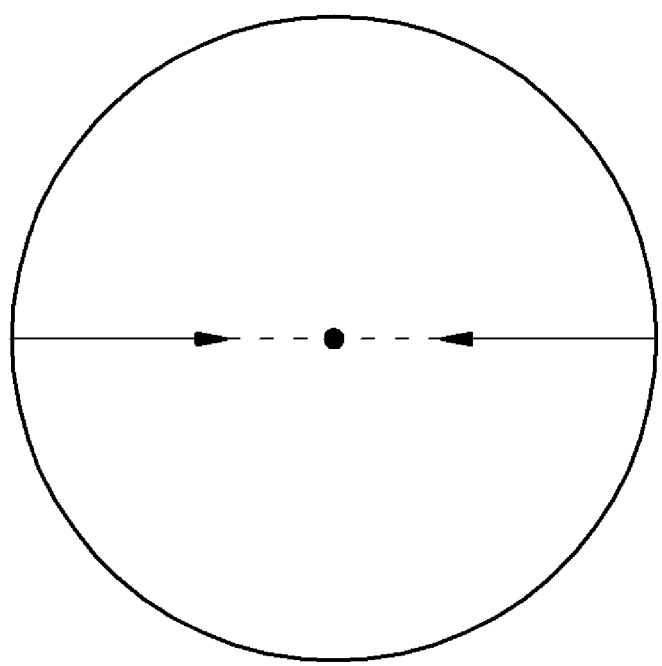
[Fig. 10]
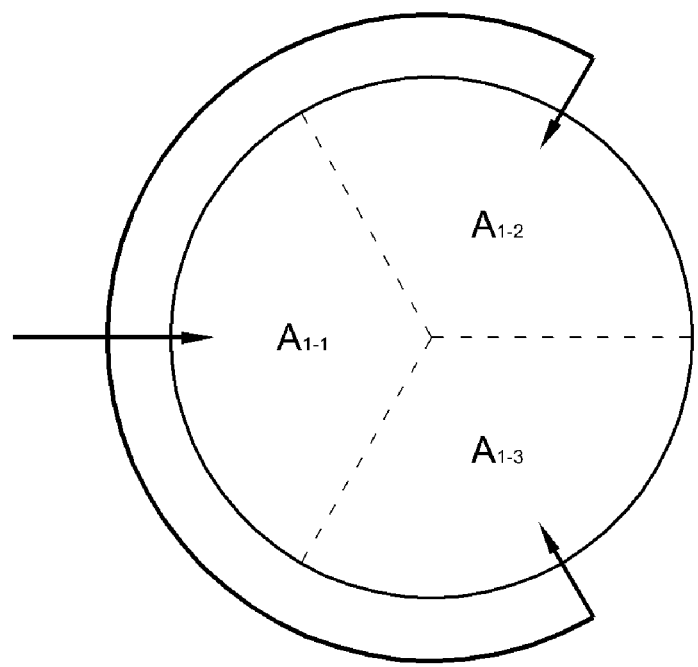

[Fig. 11]
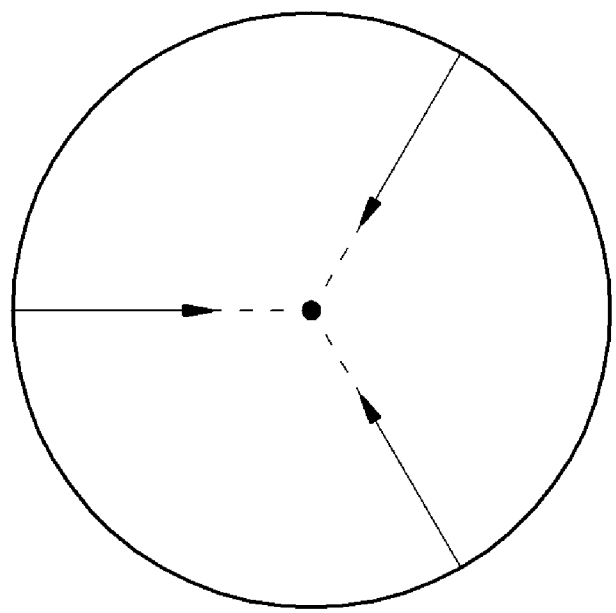
[Fig. 12]
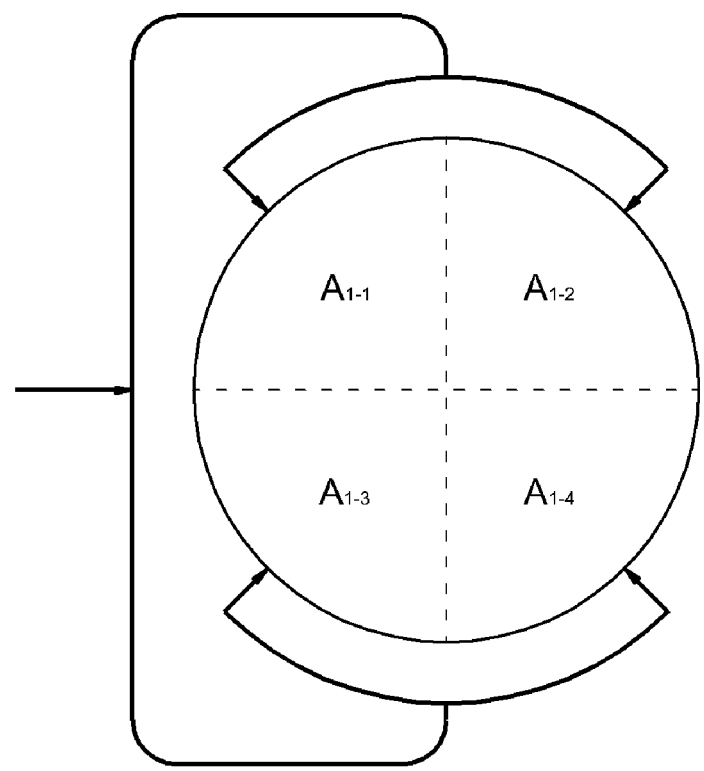

[Fig. 13]
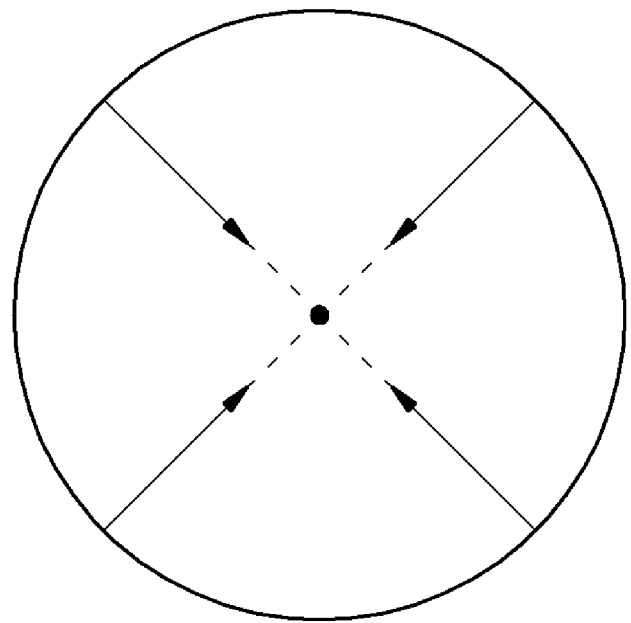
[Fig. 14]
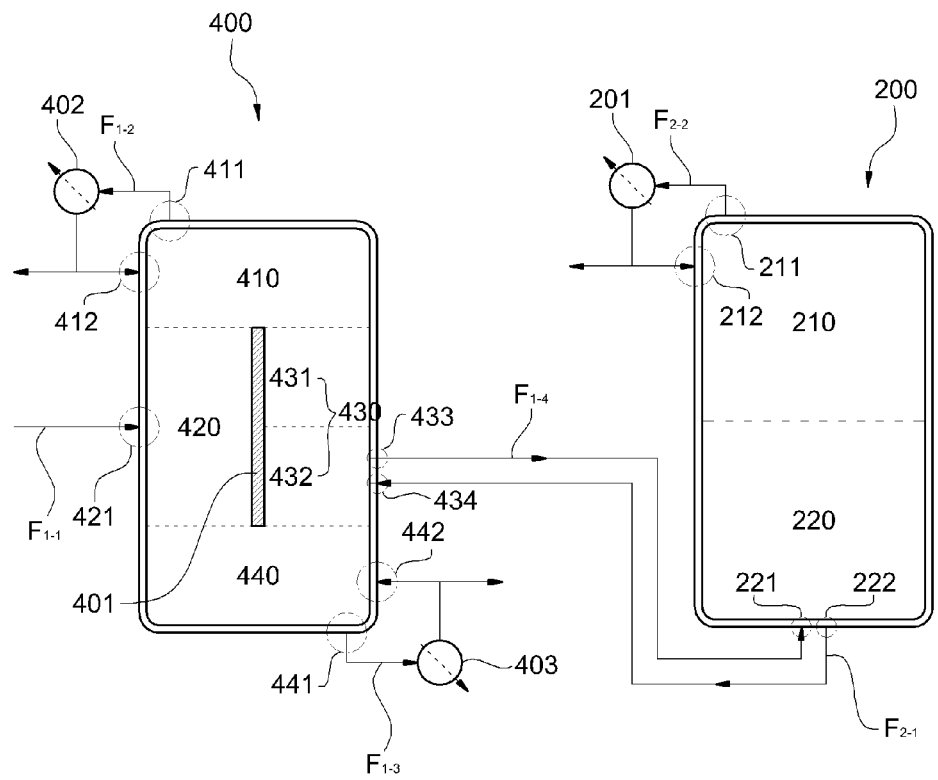

[Fig. 15]
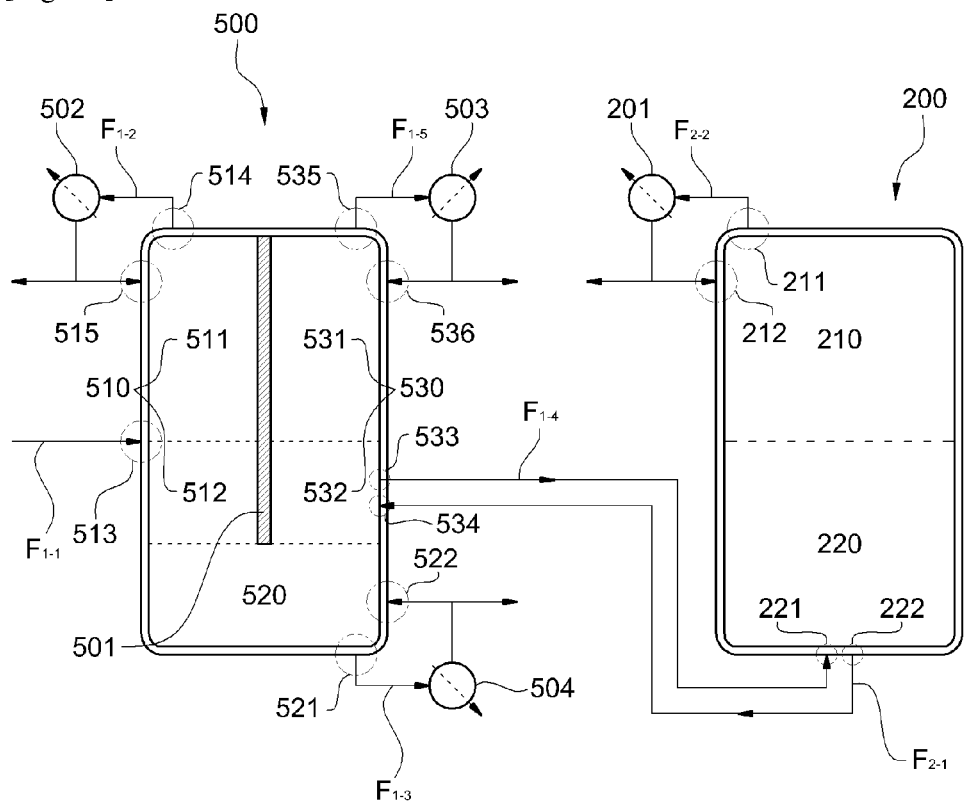
[Fig. 16]
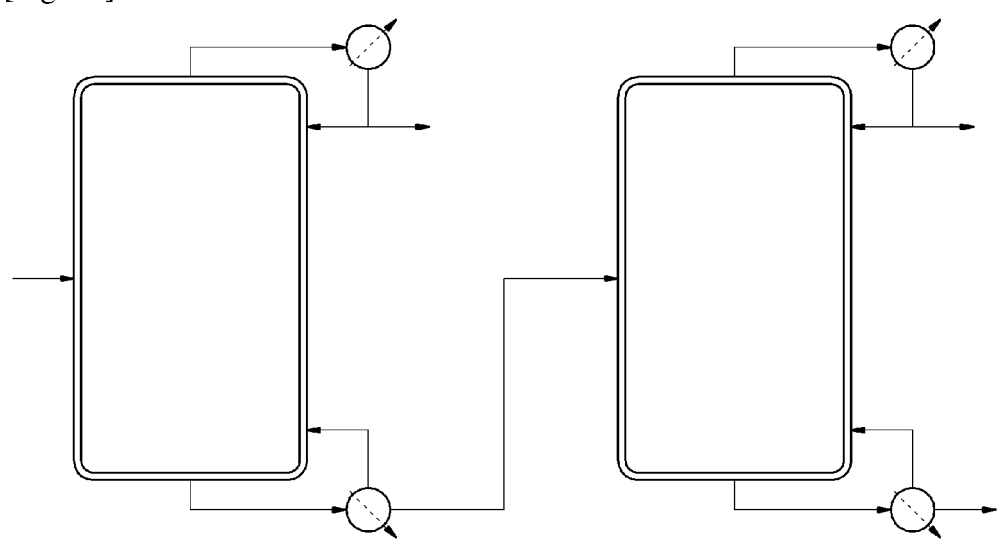

DISTILLATION APPARATUS

This application is a National Stage Entry of International Application No. PCT/KR2014/006573, filed Jul. 18, 2014, and claims the benefit of and priority to Korean Application No. 10-2013-0084496, filed on Jul. 18, 2013, Korean Application No. 10-2013-0084495, filed on Jul. 18, 2013, Korean Application No. 10-2013-0106471, filed on Sep. 5, 2013, and Korean Application No. 10-2014-0091326, filed on Jul. 18, 2014, all of which are hereby incorporated by reference in their entirety for all purposes as if fully set forth herein.

TECHNICAL FIELD

The present application relates to a distillation apparatus and a method for separating 2-ethylhexyl acrylate using the same.

BACKGROUND ART

Various raw materials such as crude oil are mixtures of various materials, for example, various compounds, and the raw materials may be usually used after being separated into each compound. A representative process from among chemical processes for separating the mixture is a distillation process.

For example, the mixture may pass through one or more distillation columns and be distilled, a part or all of the stream may pass through a condenser or a reboiler, and then flow back to the distillation column, and a high-purity compound may be obtained through the process. In general, a raw material including a material of three or more components may pass through two or more distillation columns and may be separated into each component. For example, a low boiling point component is first separated from the raw material at the upper part of a first distillation column, and an intermediate boiling point component and a high boiling point component may be separated from the raw material at the upper and lower parts of a second distillation column connected to the first distillation column. In this case, remixing of the intermediate boiling point component may occur in the lower part area of the first distillation column, and accordingly, additional energy may be consumed.

DETAILED DESCRIPTION OF THE INVENTION

Technical Problem

An object of the present application is to provide a distillation apparatus and a method for separating 2-ethylhexyl acrylate with high purity using the distillation apparatus.

Technical Solution

The present application relates to a distillation apparatus. Exemplary embodiments of the distillation apparatus may include two distillation apparatuses. A distillation apparatus according to an exemplary embodiment of the present application may be a form connected to a first distillation apparatus and a second distillation apparatus, and may minimize energy loss generated during the distillation process of a mixture, for example, a raw material including the compound of the following Formula 1, and purify the raw material by utilizing the existing distillation apparatus, thereby enhancing the economic efficiency of the process.

Hereinafter, the distillation apparatus of the present application will be described with reference to drawings, but the drawings are illustrative only, and the range of the distillation apparatus is not limited to the accompanying drawings.

FIG. 1 is a view exemplarily illustrating a distillation apparatus according to exemplary embodiments of the present application. In an example, the distillation apparatus is a distillation apparatus in which a raw material ($F_{1-1}$) including a compound of the following Formula 1 is introduced and purified.

As illustrated in FIG. 1, the distillation apparatus includes a first distillation apparatus and a second distillation apparatus. The first distillation apparatus includes a first distillation column 100 in which the raw material ($F_{1-1}$) is introduced, and the second distillation apparatus includes a second distillation column 200 which is sequentially connected to the first distillation column 100 and to which the outflow stream of the first distillation column 100 is introduced. The first distillation column 100 and the second distillation column 200 may be connected to each other by a connection route, for example, piping or tubing.

[Formula 1]

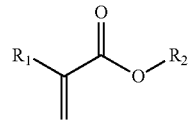

In Formula 1, $R_1$ represents hydrogen and an alkyl group having 1 to 10 carbon atoms, for example, 1 to 8, 1 to 6, or 1 to 4 carbon atoms, and R2 represents an alkyl group, for example, a linear or branched alkyl group having 1 to 24, 1 to 20, 1 to 16, 1 to 12, or 1 to 8 carbon atoms.

In an example, the component of Formula 1 is not particularly limited as long as the component is a compound which satisfies Formula 1, and may be, for example, butyl acrylate, methyl acrylate, methyl methacrylate, 2-ethylhexyl acrylate, acrylic acid, ethylene glycol, butyl alcohol, methyl alcohol, or isopropyl alcohol, preferably, 2-ethylhexyl acrylate.

The first distillation apparatus and the second distillation apparatus described above are devices which may separate a multi-component material included in the raw material ($F_{1-1}$) by the difference among the boiling points of the respective materials. In consideration of the boiling point of the component of the raw material ($F_{1-1}$) to be introduced, the component to be separated, and the like, a distillation apparatus having various forms may be used in the present application. For example, in the distillation apparatus of the present application, low boiling point and high boiling point materials are primarily separated from the first distillation column 100, and a stream including an intermediate boiling point material may be introduced into the second distillation column 200 and discharged as a product from the second distillation column 200. In the present application, the specific kind of a distillation apparatus which may be used during the process of distilling a mixture is not particularly limited, and for example, it is possible to use a distillation apparatus including a first distillation column 100 and a second distillation column 200 each having a general structure as illustrated in FIG. 1.

FIG. 2 is a view schematically illustrating a first distillation apparatus according to an exemplary embodiment of the present application. The first distillation apparatus includes the first distillation column 100, and a first condenser 101 and a reboiler 102 each connected to the first distillation column 100, as illustrated in FIG. 2. For example, the inside of the first distillation column 100 may be divided into an upper plate 110, a lower plate 130 and a middle plate 120, or into an upper part 110, a lower part 130, and a middle part 120. The term "upper plate" or "upper part" in the present specification refers to a relatively upper part in each structure of the first distillation column 100 and the second distillation column 200, and may refer to, for example, the upper part of the two areas obtained by dividing each of the first distillation column 100 and the second distillation column 200 into two parts in a height or longitudinal direction of each column. Further, the term "lower plate" or "lower part" described above refers to a relatively lower part in each structure of the first distillation column 100 and the second distillation column 200, and may refer to, for example, the lower part of the two areas obtained by dividing each of the first distillation column 100 and the second distillation column 200 into two parts in a height or longitudinal direction of each column. In addition, the term "middle plate" or "middle part" in the present specification may refer to a middle area of the three areas obtained by dividing the first distillation column 100 into three parts in a height or longitudinal direction of each distillation column, and may refer to an area between the upper part and the lower part of the first distillation column 100. In the present specification, the upper part, the lower part, and the middle part of the first distillation column 100 and the second distillation column 200 may be used as relative concepts to each other.

Furthermore, the term "condenser" used in the present specification may refer to, as a device disposed separately from the distillation column, a device for cooling by bringing a material discharged from the main body in contact with cooling water which flows in from the outside and the like. For example, the first condenser 101 of the first distillation apparatus is a device which condenses a first distillation column upper plate outflow stream ($F_{1-2}$) discharged from a first upper plate outflow part 111 of the first distillation column 100, and a second condenser 201 of the second distillation apparatus to be described below may be a device which condenses a second distillation column upper plate outflow stream ($F_{2-2}$) discharged from a second upper plate outflow part 211 of the second distillation column 200. Further, the term "reboiler" may refer to a device for re-boiling and evaporating a stream having a high boiling point as a heating device disposed outside of the distillation column. For example, the reboiler 102 of the first distillation apparatus may be a device which heats a first distillation column lower plate outflow stream ($F_{1-3}$) to be discharged from a first lower plate outflow part 131 of the first distillation column 100.

In an example, the first distillation column 100 includes a raw material inflow part 121 to which the raw material ($F_{1-1}$) is supplied, the first upper plate outflow part 111 from which a low boiling point stream is discharged, a first upper plate inflow part 112 into which a reflux stream of the stream discharged from the upper part 110 of the first distillation column is introduced, the first lower plate outflow part 131 in which a high boiling point stream is discharged from the lower part 130 of the first distillation column, a first lower plate inflow part 132 in which a reflux stream of the stream discharged from the lower part 130 of the first distillation column, a middle plate outflow part 122 in which an intermediate boiling point stream is discharged from the middle plate 120 of the first distillation column, and a middle plate inflow part 123 into which a stream discharged from a lower part 220 of the second distillation column to be described below is introduced. For example, when the raw material ($F_{1-1}$) is introduced into the raw material inflow part 121 disposed at the middle plate of the first distillation column 100, the introduced raw material ($F_{1-1}$) may be discharged while being divided into the first distillation column upper plate outflow stream ($F_{1-2}$) to be discharged from the first upper plate outflow part 111 disposed at the upper part or upper plate 110 of the first distillation column 100, a middle plate outflow stream ($F_{1-4}$) to be discharged from the middle plate outflow part 122 disposed at the middle part or middle plate 120 of the first distillation column 100, and the first distillation column lower plate outflow stream ($F_{1-3}$) to be discharged from the first lower plate outflow part 131 disposed at the lower part or lower plate 130 of the first distillation column 100, respectively. The first distillation column upper plate outflow stream ($F_{1-2}$) discharged from the first upper plate outflow part 111 passes through the first condenser 101, and a part or all of the first distillation column upper plate outflow stream ($F_{1-2}$) which has passed through the first condenser 101 may be introduced into the first upper plate inflow part 112 and flow back to the first distillation column 100 or be stored as a product. Further, the first distillation column lower plate outflow stream ($F_{1-3}$) discharged from the first lower plate outflow part 131 of the first distillation column 100 passes through the reboiler 102, and a part or all of the first distillation column lower plate outflow stream ($F_{1-3}$) which has passed through the reboiler 102 may be introduced into the first lower plate inflow part 132 and flow back to the first distillation column 100 or be stored as a product.

In an exemplary embodiment, the middle plate outflow stream ($F_{1-4}$), which is a high temperature gas-phase stream discharged from the middle plate outflow part 122 of the first distillation column 100, is introduced into the lower part 220 of the second distillation column 200, which is connected to the first distillation column 100, and thus, supplies heat required for the second distillation column lower part 220.

The term "low boiling point stream" in the present specification refers to a stream which is rich in a component having a relatively low boiling point in a raw material stream including three components having a low boiling point, an intermediate boiling point, and a high boiling point, and the low boiling point stream refers to, for example, a stream discharged from the first upper plate outflow part 111 of the first distillation column 100. The "high boiling point stream" refers to a stream which is rich in a component having a relatively high boiling point in a raw material stream including three components having a low boiling point, an intermediate boiling point, and a high boiling point, and the high boiling point stream refers to, for example, a stream which is rich in a component having a relatively high boiling point discharged from the first lower plate outflow part 131 of the first distillation column 100. The term "intermediate boiling point stream" refers to a stream which is rich in a component having a boiling point between a low boiling point component and a high boiling point component in a raw material stream including three components having a low boiling point, an intermediate boiling point, and a high boiling point, and the intermediate boiling point stream refers to, for example, a stream discharged from the middle plate outflow part 122 of the first distillation column 100. The intermediate boiling point component may be discharged from an upper part 210 of the second distillation column to be finally described below, and then stored as a product. The term "stream which is rich" refers to a stream having a higher content of each of a low boiling point component included in the stream discharged from the first upper plate outflow part 111 of the first distillation column 100, a high boiling point component included in the stream discharged from the first lower plate outflow part 131, and an intermediate boiling point component included in the stream discharged from the middle plate outflow part 122 than a content of each of the low boiling point component, the high boiling point component, and the intermediate boiling point component included in the raw material ($F_{1-1}$). For example, the term may refer to a stream in which each content of the low boiling point component included in the first distillation column upper plate outflow stream ($F_{1-2}$), the high boiling point component included in the first distillation column lower plate outflow stream ($F_{1-3}$), and the intermediate boiling point component included in the middle plate outflow stream ($F_{1-4}$) is 50 wt % or more, 80 wt % or more, 90 wt % or more, 95 wt % or more, or 99 wt % or more. In the present specification, the low boiling point stream and the first distillation column upper plate outflow stream ($F_{1-2}$) of the first distillation column 100 may be interchangeably used, the high boiling point stream and the first distillation column lower plate outflow stream ($F_{1-3}$) of the first distillation column 100 may be interchangeably used, and the intermediate boiling point stream and the middle plate outflow stream ($F_{1-4}$) of the first distillation column 100 may be interchangeably used.

As illustrated in FIG. 2, the middle plate outflow part 122 of the first distillation column 100 may be disposed in the middle part area or the middle plate 120 of the first distillation column 100, and in an example, the middle plate outflow part 122 may be disposed at a lower part than the raw material inflow part 121, that is, on the lower side. In addition, the middle plate inflow part 123 may be disposed in the middle part area or the middle plate 120, and at a lower part than the middle plate outflow part 122, that is, on the lower side. As described above, the middle plate inflow part 123 may be disposed at a lower part than the middle plate outflow part 122, and the gas/liquid may be smoothly brought into contact with each other, thereby obtaining an effect that the separation efficiency is maintained. In an example, the middle plate outflow part 122 and the middle plate inflow part 123 may be disposed at the same plate. For example, the middle plate outflow part 122 and the middle plate inflow part 123 may be disposed at the same plate inside of the middle part area 120 of the first distillation column 100, and in this case, the middle plate inflow part 123 may be disposed on the side lower than the middle plate outflow part 122 in the same plate. Accordingly, the middle plate outflow stream ($F_{1-4}$) discharged from the middle plate outflow part 122 of the first distillation column 100 and a second distillation column lower plate outflow stream ($F_{2-1}$) introduced into the middle plate inflow part 123 of the first distillation column 100 may be discharged from and introduced into the same plate of the first distillation column 100. When the middle plate outflow part 122 and the middle plate inflow part 123 are disposed at the same plate, introduction and discharge occurs at the same plate, so that the gas/liquid may be smoothly brought into contact with each other and a hydraulically smooth stream may be obtained.

In an example, the number of theoretical plates of the first distillation column 100 may be 30 to 80, 40 to 70, 25 to 50, or 45 to 60. In this case, the raw material inflow part 121 of the first distillation column 100 may be disposed in the middle part area or the middle plate 120 of the first distillation column 100, for example, at fifth to thirtieth plate, fifth to twenty fifth plate, or tenth to twentieth plate of the first distillation column 100. Furthermore, the middle plate outflow part 122 of the first distillation column 100 may be disposed on a side lower than the raw material inflow part 121, for example, at twentieth to seventy eighth plate, twenty second to forty fifth plate, thirtieth to seventy eighth plate, or fortieth to seventy fifth plate of the first distillation column 100. Further, the middle plate inflow part 123 of the first distillation column 100 is disposed at the same plate as the middle plate outflow part 122, and may be disposed on a side lower than the middle plate outflow part 122. The "number of theoretical plates" as described above refers to the number of virtual areas or plates in which two phases such as the gas phase and the liquid phase are in equilibrium with each other in a separation process using a distillation apparatus including the first distillation column 100 and the second distillation column 200.

In an example, the first upper plate outflow part 111 and the first upper plate inflow part 112 of the first distillation column 100 may be positioned at the upper part 110 of the first distillation column, and the first upper plate outflow part 111 may be positioned preferably at the column top of the first distillation column 100. Further, the first lower plate outflow part 131 and the first lower plate inflow part 132 of the first distillation column 100 may be positioned at the lower part 130 of the first distillation column, and the first lower plate outflow part 131 may be positioned preferably at the column bottom of the first distillation column 100. The "column top" as described above refers to the highest top part of the distillation column, and may be disposed at the upper plate of the above-described distillation column, and the "column bottom" as described above refers to the lowest bottom part, and may be disposed at the lower plate of the above-described distillation column. For example, the first upper plate outflow part 111 of the first distillation column 100 may be disposed at the column top of the first distillation column 100, and the first upper plate inflow part 112 of the first distillation column 100 may be disposed at the uppermost plate of the first distillation column 100, for example, the first plate of the first distillation column 100. In addition, the first lower plate outflow part 131 of the first distillation column 100 may be disposed at the column bottom of the first distillation column 100, and the first lower plate inflow part 132 of the first distillation column 100 may be disposed at the lowermost plate of the first distillation column 100, for example, eightieth, seventieth, or sixtieth plate of the first distillation column 100.

FIG. 3 is a view schematically illustrating a second distillation apparatus according to an exemplary embodiment of the present application. The second distillation apparatus includes the second distillation column 200 connected to the first distillation column 100, and the second condenser 201 connected to the second distillation column 200, as illustrated in FIG. 3. Furthermore, the second distillation column 200 includes a second lower plate inflow part 221, a second lower plate outflow part 222, a second upper plate inflow part 212 and the second upper plate outflow part 211.

In an example, the middle plate outflow stream ($F_{1-4}$), which is a high temperature gas-phase stream discharged from the middle plate outflow part 122 of the first distillation column 100, is introduced into the second lower plate inflow part 221 of the second distillation column 200, and the second distillation column lower plate outflow stream ($F_{2-1}$), which is a high temperature liquid-phase stream including a lower part product of the second distillation column 200, is discharged from the second lower plate outflow part 222, and then introduced into the middle plate inflow part 123 of the first distillation column 100.

The distillation apparatus of the present application may supply heat required for the second distillation column lower part 220 without a separate reboiler for heating a reflux stream of a stream discharged from the second distillation column lower part 220 by introducing the middle plate outflow stream ($F_{1-4}$), which is a high temperature gas-phase stream discharged from the middle plate outflow part 122 of the first distillation column 100 into the second lower plate inflow part 221 of the second distillation column 200, and an excellent purification efficiency may be exhibited without an additional supply of high temperature steam which is an external heat source supplied to the reboiler. That is, the middle plate outflow stream ($F_{1-4}$) may increase the temperature of the second distillation column lower plate outflow stream ($F_{2-1}$) which is a liquid phase stream including a lower part product of the second distillation column 200, and accordingly, the second distillation apparatus of the present application may not need a separate external heat source for heating the second distillation column lower plate outflow stream ($F_{2-1}$) of the second distillation column 200, thereby reducing costs required for the process. Further, the temperature of the second distillation column lower plate outflow stream ($F_{2-1}$) may be efficiently increased only by heat energy less than heat energy used when utilizing sensible heat of the liquid by using latent heat generated from high-temperature steam. Accordingly, the distillation apparatus of the present application may exhibit excellent economic efficiency in terms of energy efficiency and installation costs of the device. In addition, a small amount of the high boiling point material which has not been removed may be completely removed from the lower part 130 of the first distillation column by introducing the second distillation column lower plate outflow stream ($F_{2-1}$), which is a high temperature liquid-phase stream discharged from the lower part 220 of the second distillation column into the middle plate inflow part 123 of the first distillation column 100.

In an example, the second lower plate outflow part 222 and the second lower plate inflow part 221 of the second distillation column 200 may be disposed at the same plate of the second distillation column 200. Accordingly, the second distillation column lower plate outflow stream ($F_{2-1}$) discharged from the second lower plate outflow part 222 of the second distillation column 200 and the middle plate outflow stream ($F_{1-4}$) introduced into the second lower plate inflow part 221 of the second distillation column 200 may be discharged from and introduced into the same plate of the second distillation column 200. When the second lower plate outflow part 222 and the second lower plate inflow part 221 are disposed at the same plate, introduction and discharge occur at the same plate, so that the gas/liquid may be smoothly brought into contact with each other and a hydraulically smooth stream may be obtained.

In an example, the second upper plate outflow part 211 and the second upper plate inflow part 212 of the second distillation column 200 may be positioned at the upper part 210 of the second distillation column, and the second upper plate outflow part 211 may be positioned preferably at the column top of the second distillation column 200. Furthermore, the second lower plate outflow part 222 and the second lower plate inflow part 221 of the second distillation column 200 may be positioned at the lower part 220 of the second distillation column, preferably at the column bottom of the second distillation column 200. For example, the number of theoretical plates of the second distillation column 200 may be 5 to 40, preferably 10 to 30, and more preferably 15 to 25. In this case, the second upper plate outflow part 211 of the second distillation column 200 may be disposed at the column top of the second distillation column 200, and the second upper plate inflow part 212 of the second distillation column 200 may be disposed at the uppermost plate of the second distillation column 200, for example, the first plate of the second distillation column 200. Furthermore, the second lower plate outflow part 222 and the second lower plate inflow part 221 of the second distillation column 200 may be disposed at the column bottom of the second distillation column 200.

The second distillation column upper plate outflow stream ($F_{2-2}$) including an upper part product of the second distillation column 200 is discharged from the second upper plate outflow part 211 of the second distillation column 200 and passes through the second condenser 201, and a part or all of the second distillation column upper plate outflow stream ($F_{2-2}$) which has passed through the second condenser 201 is introduced into the second upper plate inflow part 212, and flows back to the second distillation column 200 or is stored as a product. The second distillation column upper plate outflow stream ($F_{2-2}$) is a stream which is rich in an intermediate boiling point component in the raw material ($F_{1-1}$) components, and may be a stream which is rich in 2-ethylhexyl acrylate in an example.

In an example, in order to perform the process of separating three components having a low boiling point, an intermediate boiling point, and a high boiling point from the raw material ($F_{1-1}$) including the three components, respectively, the raw material ($F_{1-1}$) may be introduced into the raw material inflow part 121 of the first distillation column 100 as illustrated in FIG. 1. Further, the middle plate outflow stream ($F_{1-4}$) of the first distillation column 100 may be introduced into the second lower plate inflow part 221 of the second distillation column 200. When the raw material ($F_{1-1}$) is introduced into the first distillation column 100, the low boiling point stream having a relatively low boiling point among the components included in the raw material ($F_{1-1}$) may be discharged from the first upper plate outflow part 111, the high boiling point stream having a relatively high boiling point is discharged from the first lower plate outflow part 131, and the intermediate boiling point stream may be discharged from the middle plate outflow part 122. The stream discharged from the middle plate outflow part 122 of the first distillation column 100 is introduced into the second lower plate inflow part 221 of the second distillation column 200 connected to the first distillation column 100, and a stream of the component having a relatively low boiling point among the intermediate boiling point components introduced into the second distillation column 200 is discharged from the second upper plate outflow part 211. In addition, a stream of the component having a relatively high boiling point among the components introduced into the second distillation column 200 may be discharged from the second lower plate outflow part 222 and introduced into the middle plate inflow part 123 of the first distillation column 100 connected to the second distillation column 200. In an example, when the raw material ($F_{1-1}$) including the low boiling point component, 2-ethylhexyl acrylate which is an intermediate boiling point component, and the high boiling point component is introduced into the raw material inflow part 121 of the first distillation column 100, the low boiling point component among the components of the raw material ($F_{1-1}$) is discharged into the first distillation column upper plate outflow stream ($F_{1-2}$), the discharged first distillation column upper plate outflow stream ($F_{1-2}$) passes through the first condenser 101, a part thereof may flow back to the first upper plate inflow part 112 of the first distillation column 100, and the other parts thereof may be stored as a product.

Meanwhile, the high boiling point component among the components of the raw material ($F_{1-1}$) is discharged into the first distillation column lower plate outflow stream ($F_{1-3}$) in the first lower plate outflow part 131 of the first distillation column 100, and the discharged first distillation column lower plate outflow stream ($F_{1-3}$) passes through the reboiler 102, a part thereof may flow back to the first lower plate inflow part 132 of the first distillation column 100, and the other parts thereof may be produced as a product. Furthermore, the middle plate outflow stream ($F_{1-4}$) including the intermediate boiling point component among the components of the raw material ($F_{1-1}$) is discharged from the middle plate outflow part 122 of the first distillation column 100, and thus may be introduced into the second lower plate inflow part 221 of the second distillation column 200 connected to the first distillation column 100. Further, a stream introduced into the second lower plate inflow part 221 of the second distillation column 200 may be separated into the second distillation column upper plate outflow stream ($F_{2-2}$) and the second distillation column lower plate outflow stream ($F_{2-1}$) and discharged. The upper part product of the second distillation column 200, which is a stream including a relatively low boiling point component among the components included in the stream introduced into the second distillation column 200, for example, a part or all of the second distillation column upper plate outflow stream ($F_{2-2}$) including 2-ethylhexyl acrylate is discharged from the second upper plate outflow part 211, and the discharged second distillation column upper plate outflow stream ($F_{2-2}$) passes through the second condenser 201, a part thereof flows back to the second upper plate inflow part 212 of the second distillation column 200, and the other parts thereof may be stored as a product. Meanwhile, the second distillation column lower plate outflow stream ($F_{2-1}$) including the lower part product of the second distillation column 200, which is a stream including a relatively high boiling point component among the components included in the stream introduced into the second distillation column 200 may be introduced into the middle plate inflow part 123 of the first distillation column 100 connected to the second distillation column 200. In this case, the temperature of the upper part 110 of the first distillation column may be 80 to 115° C., 85 to 100° C., or 90 to 105° C., and the temperature of the lower part 130 of the first distillation column may be 120 to 160° C., 130 to 155° C., or 135 to 147° C. In addition, the reflux ratio of the first distillation column upper plate outflow stream ($F_{1-2}$) which flows back to the first upper plate outflow part 111 of the first distillation column 100 in the first distillation column upper plate outflow stream ($F_{1-2}$) of the first distillation column 100 may be 1 to 10, and may be preferably 1.2 to 7.0 or 1.5 to 4.5 from a thermodynamic viewpoint. The reflux ratio of the first distillation column lower plate outflow stream ($F_{1-3}$) which flows back to the first lower plate inflow part 132 of the first distillation column 100 in the first distillation column lower plate outflow stream ($F_{1-3}$) of the first distillation column 100 may be 1 to 30, and may be preferably 5 to 25 or 10 to 20 from the thermodynamic viewpoint. Furthermore, the temperature of the upper part 210 of the second distillation column may be 100 to 130° C., 104 to 125° C., or 108 to 120° C., and the temperature of the lower part 220 of the second distillation column may be 120 to 150° C., 120 to 140° C., or 123 to 133° C. Further, the reflux ratio of the second distillation column upper plate outflow stream ($F_{2-2}$) which flows back to the second upper plate inflow part 212 of the second distillation column 200 among the second distillation column upper plate outflow stream ($F_{2-2}$) of the second distillation column 200 may be 0.01 to 5.0, and may be preferably 0.05 to 1.0 or 0.1 to 2.0 from the thermodynamic viewpoint. The term "reflux ratio" used in the present specification refers to a ratio of the flow rate to flow back with respect to the outflow flow rate to be discharged from the first distillation column 100.

FIG. 4 is a view exemplarily illustrating a distillation apparatus according to an exemplary embodiment of the present application.

As illustrated in FIG. 4, the distillation apparatus according to an exemplary embodiment of the present application may include a heater which pre-heats the raw material ($F_{1-1}$).

The heater 300 may be disposed at the front plate of a part into which the raw material of the first distillation column 100 is introduced, and may heat the raw material ($F_{1-1}$) to be introduced into the raw material inflow part 121. Accordingly, since the temperature of the raw material ($F_{1-1}$) may be increased before the raw material ($F_{1-1}$) is introduced into the first distillation column 100, the size of the distillation apparatus used for the purification can be minimized while minimizing the energy loss generated during the separation process. In an example, the raw material ($F_{1-1}$) at a temperature of 20 to 40° C. may be heated to a temperature of 50 to 110° C., preferably 60 to 100° C., or 70 to 90° C. by the heater 300. The preheated raw material ($F_{1-1}$) may be introduced into the raw material inflow part 121 of the first distillation column 100, and the components included in the raw material ($F_{1-1}$) may be discharged while being divided into the first distillation column upper plate outflow stream ($F_{1-2}$), the first distillation column lower plate outflow stream ($F_{1-3}$), and the middle plate outflow stream ($F_{1-4}$) according to the boiling points thereof. As described above, when the raw material ($F_{1-1}$) is pre-heated by the heater 300, the raw material ($F_{1-1}$) may be preheated through low-pressure steam, and it is possible to reduce the amount of high-pressure steam consumed, which is used in the reboiler 102 in order to heat a part of stream to flow back to the first lower plate inflow part 132 in the first distillation column lower plate outflow stream ($F_{1-3}$) of the first distillation column 100 by introducing the preheated raw material ($F_{1-1}$) into the first distillation column 100. The detailed contents on the process in which the raw material ($F_{1-1}$) is separated in the first distillation column 100 is the same as that described above, and thus will be omitted.

Various devices publicly known in the art may be used as long as the heater 300 is a device which may increase the temperature of the raw material ($F_{1-1}$), and a device may be appropriately selected and used according to the kind and temperature of a target raw material ($F_{1-1}$), but is not particularly limited.

FIG. 5 is a view exemplarily illustrating a distillation apparatus according to another exemplary embodiment of the present application.

As illustrated in FIG. 5, the distillation apparatus of the present application may additionally include a first heat exchanger 301. The first heat exchanger 301 is disposed at the front plate of the first condenser 101 of the first distillation column 100, and may heat-exchange the first distillation column upper plate outflow stream ($F_{1-2}$) with the raw material ($F_{1-1}$). The first heat exchanger 301 may be disposed to be directly or indirectly connected to a piping or tubing through which the first distillation column upper plate outflow stream ($F_{1-2}$) of the first distillation column 100 flows. In an example, the first heat exchanger 301 may be directly connected to the piping or tubing through which the first distillation column upper plate outflow stream ($F_{1-2}$) of the first distillation column 100 flows, thereby efficiently heat-exchanging the raw material ($F_{1-1}$) and the first distillation column upper plate outflow stream ($F_{1-2}$) of the first distillation column 100. For example, the first heat exchanger 301 may be disposed at the front plate of the first condenser 101, and may be preferably directly connected to a piping or tubing through which the raw material ($F_{1-1}$) flows, thereby heat-exchanging the first distillation column upper plate outflow stream ($F_{1-2}$) with the raw material ($F_{1-1}$) before being introduced into the first condenser 101.

As described above, in the first distillation column 100 which additionally includes the first heat exchanger 301, the low boiling point stream discharged from the first distillation column 100 passes through the first heat exchanger 301, and supplies the first heat exchanger 301 with heat. Accordingly, the first distillation column upper plate outflow stream ($F_{1-2}$) discharged from the first distillation column 100 may flow back to the first distillation column 100 at a relatively low temperature. When the first distillation column 100 including the first heat exchanger 301 is used as described above, it is possible to reduce the amount of heat to condense the first distillation column upper plate outflow stream ($F_{1-2}$) discharged from the first upper plate outflow part 111. Accordingly, the costs required for a condensing process may be reduced by decreasing the amount of cooling water used in the condensing process using the first condenser 101.

Further, the first heat exchanger 301 may heat-exchange the raw material ($F_{1-1}$) with the first distillation column upper plate outflow stream ($F_{1-2}$) which is at a relatively high temperature before being introduced into the first distillation column 100, thereby increasing the temperature of the raw material ($F_{1-1}$). Accordingly, it is possible to reduce the amount of steam consumed to be used in the reboiler 102 in order to heat a part of the stream flowing back to the first lower plate inflow part 132 in the first distillation column lower plate outflow stream ($F_{1-3}$) discharged from the first distillation column 100. In addition, the temperature of the raw material may be efficiently increased only by heat energy less than the case where sensible heat of the liquid is utilized by using latent heat generated from the high-temperature steam. As described above, energy efficiency may be increased by utilizing waste heat discarded, and the compound may be separated with high purity while minimizing the size of the distillation column.

For example, the raw material ($F_{1-1}$) at a temperature of 20 to 40° C. may be heat-exchanged with the first distillation column upper plate outflow stream ($F_{1-2}$) at a temperature of 80 to 115° C. in the first heat exchanger 301. Accordingly, the raw material ($F_{1-1}$) may be heated to a temperature of 50 to 110° C., preferably 60 to 100° C., and more preferably 70 to 90° C., and then may be introduced into the raw material inflow part 121 of the first distillation column 100. Furthermore, the first distillation column upper plate outflow stream ($F_{1-2}$) at 80 to 115° C., which has been heat-exchanged with the raw material ($F_{1-1}$), passes through the first condenser 101, and then is condensed at 25 to 40° C., and may be stored as a product or flow back to the first upper plate inflow part 112.

FIG. 6 is a view exemplarily illustrating a distillation apparatus according to still another exemplary embodiment of the present application.

As illustrated in FIG. 6, the distillation apparatus of the present application may additionally include a second heat exchanger 302. The second heat exchanger 302 is disposed at the front plate of the second condenser 201 of the second distillation column 200, and may heat-exchange the second distillation column upper plate outflow stream ($F_{2-2}$) with the raw material ($F_{1-1}$). The second heat exchanger 302 may be disposed to be directly or indirectly connected to a piping or tubing through which the second distillation column upper plate outflow stream ($F_{2-2}$) of the second distillation column 200 flows. In an example, the second heat exchanger 302 may be directly connected to the piping or tubing through which the second distillation column upper plate outflow stream ($F_{2-2}$) of the second distillation column 200 flows, thereby efficiently heat-exchanging the raw material ($F_{1-1}$) and the second distillation column upper plate outflow stream ($F_{2-2}$). For example, the second heat exchanger 302 may be disposed at the front plate of the second condenser 201, and may be preferably directly connected to a piping or tubing through which the raw material ($F_{1-1}$) flows, thereby heat-exchanging the second distillation column upper plate outflow stream ($F_{2-2}$) with the raw material ($F_{1-1}$) before being introduced into the second condenser 201.

As described above, by additionally including the second heat exchanger 302, the intermediate boiling point stream discharged from the second distillation column 200 passes through the second heat exchanger 302, and supplies the second heat exchanger 302 with heat. Accordingly, the second distillation column upper plate outflow stream ($F_{2-2}$) discharged from the second distillation column 200 may flow back to the second distillation column 200 at a relatively low temperature. When the second distillation column 200 including the second heat exchanger 302 is used as described above, it is possible to reduce the amount of heat to condense the second distillation column upper plate outflow stream ($F_{2-2}$) discharged from the second upper plate outflow part 211. Accordingly, the costs required for a condensing process may be reduced by decreasing the amount of cooling water used in the condensing process using the second condenser 201. Further, the second heat exchanger 302 may heat-exchange the raw material ($F_{1-1}$) with the second distillation column upper plate outflow stream ($F_{2-2}$) discharged from the second distillation column 200, which is at a relatively high temperature before being introduced into the first distillation column 100, thereby increasing the temperature of the raw material ($F_{1-1}$). For example, the raw material ($F_{1-1}$) at a temperature of 20 to 40° C. may be heat-exchanged with the second distillation column upper plate outflow stream ($F_{2-2}$) at a temperature of 100 to 130° C. in the second heat exchanger 302. Accordingly, the raw material ($F_{1-1}$) may be heated to a temperature of 50 to 120° C., 60 to 120° C., or 90 to 110° C., and then may be introduced into the raw material inflow part 121 of the first distillation column 100. In addition, the second distillation column upper plate outflow stream ($F_{2-2}$) at 100 to 130° C., which has been heat-exchanged with the raw material ($F_{1-1}$), passes through the second condenser 201, and then is condensed at 40 to 90° C., and may be stored as a product or flow back to the second upper plate inflow part 212. The specific contents on the distillation apparatus including the second heat exchanger 302 are the same as the contents on the above-described distillation apparatus including the first heat exchanger 301, and thus, will be omitted.

In another exemplary embodiment of the present application, one or more of the raw material inflow part 121, the first upper plate inflow part 112, the middle plate outflow part 122, the middle plate inflow part 123, and the first lower plate inflow part 132 of the first distillation column 100, and the second lower plate outflow part 222, the second lower plate inflow part 221, and the second upper plate inflow part 212 of the second distillation column 200 is formed of two or more openings disposed to be separated from each other. Accordingly, channeling occurring during the purification process of the raw material ($F_{1-1}$) may be blocked, thereby minimizing energy loss and enhancing the economic efficiency of the process. The term "channeling" in the present specification refers to a phenomenon in which contact of a mixture of steam and liquid in a distillation column does not smoothly occur, or a liquid inclination phenomenon in which a fluid flows lopsidedly toward a specific part of a wall surface of a dividing wall-type distillation column, and channeling is responsible for a significant deterioration in efficiency of separating raw materials and additional energy consumption.

In an example, the two or more openings may be disposed such that a stream introduced into or discharged from the first distillation column 100 and/or the second distillation column 200 may be introduced in two or more directions or discharged in two or more directions.

In an exemplary embodiment, the first distillation column 100 and/or the second distillation column 200 may include two or more small areas which equally divide a horizontal cross section. FIG. 7 is a view illustrating the cross section of the first distillation column 100, which is in parallel with the ground surface. As illustrated in FIG. 7, the first distillation column 100 may include an arbitrary small area which divides the horizontal cross section of the first distillation column 100 into an equal area, for example, a plurality of small areas ($A_{1-1}$, $A_{1-2}$, $A_{1-3}$, and $A_{1-4}$). The same may also be applied to the second distillation column 200.

In an example, two or more openings may be formed to be separated from each other in one or more of the raw material inflow part 121, the first upper plate inflow part 112, the middle plate outflow part 122, the middle plate inflow part 123, and the first lower plate inflow part 132 of the first distillation column 100, and the two or more openings may be each positioned in two or more small areas which equally divide the horizontal cross-sectional area of the first distillation column 100. The fact that the two or more openings "may be each disposed" as described above may mean that in the areas which are divided as equally as the number of the openings, one opening may be each disposed in one area. FIG. 8 is a view exemplarily illustrating the cross section of the first distillation column 100 in which two or more openings are formed according to the present application, which is in parallel with the ground surface. For example, as divided by a virtual dotted line in FIG. 8, the cross section of the first distillation column 100 may be divided into two equal small areas ($A_{1-1}$ and $A_{1-2}$), and when two openings are formed to be separated from each other in one or more of the raw material inflow part 121, the first upper plate inflow part 112, the middle plate outflow part 122, the middle plate inflow part 123, and the first lower plate inflow part 132 of the first distillation column 100, one of the two openings is disposed at one small area ($A_{1-1}$) of the small area divided into two and the other opening is disposed at the other small area ($A_{1-2}$), which is adjacent to the area in which the one opening is disposed, thereby disposing each one opening at each area.

In the case of the first distillation column 100 in which one opening is formed in the raw material inflow part 121, the first upper plate inflow part 112, the middle plate outflow part 122, the middle plate inflow part 123, and the first lower plate inflow part 132, a raw material or reflux stream is supplied in only one direction, or the middle plate inflow and outflow streams are introduced or discharged in only one direction, and in this case, channeling may occur. However, when two or more openings are formed in one or more of the raw material inflow part 121, the first upper plate inflow part 112, the middle plate outflow part 122, the middle plate inflow part 123, and the first lower plate inflow part 132 of the first distillation column 100, the raw material ($F_{1-1}$), the reflux stream, the middle plate outflow and/or inflow stream may be equally introduced or equally discharged in two or more directions, thereby preventing the channeling from occurring.

In the first distillation column 100 according to the present application, channeling may be effectively suppressed by controlling the position of each opening and the flow rate and direction of stream introduced into or discharged from each opening depending on the number of two or more openings. For example, when two openings are formed to be separated from each other in one or more of the raw material inflow part 121, the first upper plate inflow part 112, the middle plate outflow part 122, the middle plate inflow part 123, and the first lower plate inflow part 132 of the first distillation column 100, the two openings may be each disposed in the two areas ($A_{1-1}$ and $A_{1-2}$) which equally divide the cross section of the first distillation column 100 in parallel with the ground surface, as described above. Specifically, as illustrated in FIG. 9, the two openings may be disposed in opposite sides with respect to a central point of the cross section, and the raw material ($F_{1-1}$) may be each introduced into the two raw material inflow parts 121, so that it is possible to efficiently suppress channeling from occurring while the raw material ($F_{1-1}$) is introduced. In an example, when two openings are formed to be separated from each other in one or more of the raw material inflow part 121, the first upper plate outflow part 111, the first upper plate inflow part 112, the middle plate outflow part 122, the middle plate inflow part 123, and the first lower plate inflow part 132, an angle, which an extension line extending from any one of the two openings to the center of the distillation column and an extension line extending from the other opening to the center of the distillation column form, may be, for example, 175° to 185°, 177° to 183°, or 179° to 181°, as illustrated in FIG. 9, and channeling may be maximally blocked by controlling the angle to the range.

FIG. 10 is a view exemplarily illustrating the cross section of the first distillation column 100 in which three openings are formed according to the present application, which is in parallel with the ground surface. As illustrated in FIG. 10, for example, three openings may be formed to be separated from each other in one or more of the raw material inflow part 121, the first upper plate inflow part 112, the middle plate outflow part 122, the middle plate inflow part 123, and the first lower plate inflow part 132 of the first distillation column 100, and the three openings may be each disposed in the three areas ($A_{1-1}$, $A_{1-2}$, and $A_{1-3}$) which equally divide the cross section of the first distillation column 100 in parallel with the ground surface. Specifically, as illustrated in FIG. 10, the three openings may be disposed at certain intervals, and may be disposed such that the stream of fluid may be each introduced into or discharged from the three openings. In an example, when three openings are formed to be separated from each other in one or more of the raw material inflow part 121, the first upper plate inflow part 112, the middle plate outflow part 122, the middle plate inflow part 123, and the first lower plate inflow part 132, an angle, which an extension line extending from any one of the three openings to the center of the distillation column and an extension line extending from the other two openings to the center of the distillation column form, may be, for example, 115° to 125°, 117° to 123°, or 119° to 121°, as illustrated in FIG. 11, and channeling may be maximally blocked by controlling the angle to the range.

FIG. 12 is a view exemplarily illustrating the cross section of the first distillation column 100 in which four openings are formed according to the present application, which is in parallel with the ground surface. As illustrated in FIG. 12, for example, four openings may be formed to be separated from each other in one or more of the raw material inflow part 121, the first upper plate inflow part 112, the middle plate outflow part 122, the middle plate inflow part 123, and the first lower plate inflow part 132 of the first distillation column 100, and the four openings may be each disposed in the four areas ($A_{1-1}$, $A_{1-2}$, $A_{1-3}$, and $A_{1-4}$) which equally divide the cross section of the first distillation column 100 in parallel with the ground surface. Specifically, as illustrated in FIG. 12, the four openings may be disposed at certain intervals, and may be disposed such that the stream of fluid may be each introduced into or discharged from the four openings. In an example, when four openings are formed to be separated from each other in one or more of the raw material inflow part 121, the first upper plate inflow part 112, the middle plate outflow part 122, the middle plate inflow part 123, and the first lower plate inflow part 132, an angle, which an extension line extending from any one of the four openings to the center of the distillation column and an extension line extending from two openings adjacent to the one opening to the center of the distillation column form, may be, for example, 85° to 95°, preferably 87° to 93°, and more preferably 89° to 91°, as illustrated in FIG. 13, and channeling may be maximally blocked by controlling the angle to the range.

When the stream of fluid introduced into or discharged from the first distillation column 100 is supplied or discharged in two or more directions, it is possible to uniformly maintain the stream of a liquid which drops onto the lower area of plates at which the raw material inflow part 121, the first upper plate inflow part 112, the middle plate outflow part 122, the middle plate inflow part 123, and the first lower plate inflow part 132 of the first distillation column 100 are disposed, thereby enhancing the purification efficiency. That is, when the raw material inflow part 121, the first upper plate inflow part 112, the middle plate outflow part 122, the middle plate inflow part 123, and the first lower plate inflow part 132 of the first distillation column 100, in which two or more openings are formed, satisfy the aforementioned conditions, it is possible to effectively block channeling from occurring while each stream is introduced, and the design and operation convenience of the distillation apparatus are excellent, so that the raw material ($F_{1-1}$) may be separated with high efficiency.

As illustrated in FIGS. 9, 11, and 13, the first distillation column 100 of the present application may allow all the vector components of the inflow speed projected onto the cross section of the first distillation column 100, which is in parallel with the ground surface to be directed toward the central point of the cross section. Specifically, the dimensions of the flow rate and the inflow speed to be introduced through the two or more openings are the same as each other, and a value obtained by each adding up the products of vector components of the flow rate (F) of the stream of fluid and the inflow speed projected onto the cross section may be 0 (zero). As described above, when each of the sums of the products of the flow rate of the stream of fluid and the vector component of the inflow speed projected onto the cross section through two or more openings is offset to 0 (zero), channeling due to the stream of two or more fluids may be effectively blocked. The term "flow rate (F)" as described above refers to a flow rate (volume per unit time) to be introduced through each inflow part, and the term "vector component of the inflow speed" refers to a vector component in which the vector of the inflow speed (distance per unit time) through each inflow part is projected onto the cross section of the distillation column, which is in parallel with the ground surface.

In one exemplary embodiment, two or more openings may be formed to be separated from each other in the raw material inflow part 121 of the first distillation column 100, and the two or more openings may be each disposed at two or more small areas which equally divide the cross section of the first distillation column 100 in parallel with the ground surface. In the case of a distillation column in which one opening is formed in the raw material inflow part 121, a liquid stream, which drops onto a lower area of the supply plate of the distillation column, does not uniformly drop, and channeling may occur, and accordingly, the separation efficiency of the raw material ($F_{1-1}$) may deteriorate. However, when two or more openings are formed in the raw material inflow part 121 of the first distillation column 100, channeling is suppressed by uniformly maintaining the stream of the liquid which drops onto the raw material supply plate lower part of the first distillation column 100, so that the raw material ($F_{1-1}$) may be efficiently separated. In this case, the two or more openings may be disposed at the same plate inside of the first distillation column 100, preferably, on the same plane in parallel with the ground surface. Accordingly, the raw material ($F_{1-1}$) to be each introduced into the two or more openings may be introduced such that a hydraulically smooth stream is obtained, thereby effectively preventing channeling. For example, the two or more raw material inflow parts 121 may be disposed at the same plate of the first distillation column 100, and in the case of a first distillation column 100 in which the number of theoretical plates is 30 to 80, 40 to 70, or 45 to 60, the raw material inflow part 121 which forms the two or more openings may be disposed at fifth to thirtieth plate, preferably fifth to twenty fifth plate, and more preferably tenth or twentieth plate of the first distillation column 100. Furthermore, when the raw material ($F_{1-1}$) is each introduced into the raw material inflow part 121 in which two or more openings are formed at the same flow rate, channeling is easily blocked and the operation convenience of the distillation column is excellent, thereby separating the raw material ($F_{1-1}$) with high efficiency.

In one exemplary embodiment, two or more openings may be formed to be separated from each other in the first upper plate inflow part 112 of the first distillation column 100, and the two or more openings may be each disposed at two or more small areas which equally divide the horizontal cross section of the first distillation column 100. In a dividing wall-type distillation column 100 in which one opening is formed in the first upper plate inflow part 112, channeling may occur while the reflux stream of the first distillation column upper plate outflow stream ($F_{1-2}$) is introduced into the first distillation column 100 in one direction. Accordingly, the separation efficiency of the raw material ($F_{1-1}$) may deteriorate, and in this case, additional energy is consumed in order to maintain the concentration of the low boiling point material in the first distillation column upper plate outflow stream ($F_{1-2}$). However, when two or more openings are formed in the first upper plate inflow part 112 of the first distillation column 100, the reflux stream of the first distillation column upper plate outflow stream ($F_{1-2}$) is introduced into the first distillation column in two or more directions, and thus, channeling is suppressed, thereby efficiently separating the raw material ($F_{1-1}$). In an example, the two or more first upper plate inflow parts 112 may be disposed on the same plate in the upper plate of the first distillation column 100, preferably, on the same plane in parallel to the ground surface, and in the case of a first distillation column 100 in which the number of theoretical plates is 30 to 80, 40 to 70, or 45 to 60, the first upper plate inflow part 112 in which the two or more openings are formed may be disposed at the uppermost plate, for example, the first plate of the first distillation column 100.

Further, two or more openings may be formed to be separated from each other in the first lower plate inflow part 132 of the first distillation column 100, and the two or more openings may be each disposed at two or more small areas which equally divide the horizontal cross section of the first distillation column 100. In this case, the first distillation column lower plate outflow stream ($F_{1-3}$) which has passed through the reboiler 102 may flow back in two or more directions, thereby enhancing the separation efficiency of the raw material ($F_{1-1}$). For example, the first lower plate inflow part 132 in which the two or more openings are formed may be disposed at the same plate in the lower plate of the first distillation column 100, preferably, on the same plane in parallel with the ground surface, and in the case of a first distillation column 100 in which the number of theoretical plates is 30 to 80, 40 to 70, or 45 to 60, the first lower plate inflow part 132 in which the two or more openings are formed may be disposed at the lowermost plate, for example, the eightieth plate, the seventieth plate, or the sixtieth plate, of the first distillation column 100.

In one exemplary embodiment, two or more openings may be formed to be separated from each other in the middle plate outflow part 122 of the first distillation column 100, and the two or more openings may be each disposed at two or more small areas which equally divide the horizontal cross section of the first distillation column 100. In this case, the middle plate outflow stream ($F_{1-4}$) discharged from the middle plate outflow part 122 of the first distillation column 100 may be discharged in two or more directions, thereby smoothly maintaining the hydraulic stream. For example, the middle plate outflow part 122 in which the two or more openings are formed may be disposed at the same plate in the middle plate of the first distillation column 100, preferably, on the same plane in parallel with the ground surface, and may also be disposed on a side lower than the raw material inflow part 121. For example, in the case of a first distillation column 100 in which the number of theoretical plates is 30 to 80, 40 to 70, or 45 to 60, the middle plate outflow part 122 may be disposed at twentieth to seventy eighth plate, twenty second to forty fifth plate, thirtieth to seventy eighth plate, or fortieth to seventy fifth plate of the first distillation column 100.

In one exemplary embodiment, two or more openings may be formed to be separated from each other in the middle plate inflow part 123 of the first distillation column 100, and the two or more openings may be each disposed at two or more small areas which equally divide the horizontal cross section of the first distillation column 100. In this case, the second distillation column lower plate outflow stream ($F_{2-1}$) introduced into the middle plate inflow part 123 of the first distillation column 100 from the second distillation column 200 may be introduced in two or more directions, thereby enhancing the separation efficiency of the raw material ($F_{1-1}$). For example, the middle plate inflow part 123 in which the two or more openings are formed may be disposed at the same plate in the middle plate of the first distillation column 100, preferably, on the same plane in parallel with the ground surface, and may also be disposed at the plate at which the above-described middle plate outflow part 122 is disposed. In addition, in this case, the middle plate inflow part 123 may be disposed on a side lower than the middle plate outflow part 122.

The specific contents on the first upper plate inflow part 112, the first lower plate inflow part 132, the middle plate outflow part 122, and the middle plate inflow part 123 in which the two or more openings are formed are the same as those described above on the two or more raw material inflow parts 121, and thus, will be omitted.

In another exemplary embodiment of the present application, the second distillation column 200 may include two or more small areas which equally divide the horizontal cross section. At this time, two or more openings may be formed to be separated from each other in one or more of the second upper plate inflow part 212, the second lower plate outflow part 222, and the second lower plate inflow part 221 of the second distillation column 200, and the two or more openings may be each disposed in two or more small areas which equally divide the horizontal cross section of the second distillation column 200.

In one exemplary embodiment, two or more openings may be formed to be separated from each other in the second lower plate outflow part 222 of the second distillation column 200, and the two or more openings may be each disposed in two or more small areas which equally divide the horizontal cross section of the second distillation column 200. In this case, the second distillation column lower plate outflow stream ($F_{2-1}$) discharged from the second lower plate outflow part 222 of the second distillation column 200 may be discharged in two or more directions, and accordingly, the hydraulic stream inside of the second distillation column 200 may be smoothly maintained. For example, the second lower plate outflow part 222 in which the two or more openings are formed may be disposed at the same plate in the lower plate of the second distillation column 200, preferably at the column bottom of the second distillation column 200.

Two or more openings may be formed to be separated from each other in the second lower plate inflow part 221 of the second distillation column 200, and the two or more openings may be each disposed in two or more small areas which equally divide the horizontal cross section of the second distillation column 200. In this case, the middle plate outflow stream ($F_{1-4}$) introduced into the second lower plate inflow part 221 of the second distillation column 200 from the first distillation column 100 may be introduced in two or more directions. Accordingly, channeling occurring while the middle plate outflow stream ($F_{1-4}$) is introduced into the second lower plate inflow part 221 of the second distillation column 200 may be suppressed, so that the separation efficiency may be enhanced. For example, the second lower plate inflow part 221 in which the two or more openings are formed may be disposed at the same plate in the lower plate of the second distillation column 200, preferably at the column bottom of the second distillation column 200.

Two or more openings may be formed to be separated from each other in the second upper plate inflow part 212 of the second distillation column 200, and the two or more openings may be each disposed in two or more small areas which equally divide the horizontal cross section of the second distillation column 200. In this case, the second distillation column upper plate outflow stream ($F_{2-2}$) which has passed through the second condenser 201 may flow back in two or more directions, thereby enhancing the separation efficiency of the raw material ($F_{1-1}$). For example, the second upper plate inflow part 212 in which the two or more openings are formed may be disposed at the same plate in the upper plate of the second distillation column 200, preferably, on the same plane in parallel with the ground surface, and in the case of a second distillation column 200 in which the number of theoretical plates is 5 to 40, 10 to 30, or preferably 15 to 25, the second upper plate inflow part 212 in which the two or more openings are formed may be disposed at the uppermost plate, for example, the first plate, of the second distillation column 200.

The specific contents on the second lower plate outflow part 222, the second lower plate inflow part 221, and the second upper plate inflow part 212 of the second distillation column 200 in which the two or more openings are formed are the same as those described above on the raw material inflow part 121 in which the two or more openings are formed, and thus, will be omitted.

FIG. 14 is a view exemplarily illustrating a distillation apparatus according to yet another exemplary embodiment of the present application.

As illustrated in FIG. 14, the distillation apparatus includes a first distillation apparatus and a second distillation apparatus, and a first distillation column 400 included in the first distillation apparatus may be a dividing wall-type distillation column 400 including a dividing wall 401 therein. The dividing wall-type distillation column 400 is a device designed to distill a raw material ($F_{1-1}$) including three components having a low boiling point, and intermediate boiling point, and a high boiling point, and a device similar to a so-called thermally coupled distillation column (Petlyuk column) from the thermodynamic viewpoint. The thermally coupled distillation column is designed to primarily separate low boiling point and high boiling point materials from a preliminary separator, and separate each of low boiling point, intermediate boiling point, and high boiling point materials from a main separator. In this regard, the dividing wall-type distillation column 400 is a type in which the preliminary separator is integrated into the main separator by disposing the dividing wall 401 inside of the column. In the distillation apparatus of the present application, low boiling point, intermediate boiling point, and high boiling point materials are primarily separated from the first distillation column 400 which is a dividing wall-type distillation column, and a middle plate outflow stream ($F_{1-4}$) including the intermediate boiling point material is introduced into the second distillation column 200, and then may be purified.

For example, the inside of the first distillation column 400 is divided by the dividing wall 401, and as divided by virtual dotted lines in the drawing, the inside of the first distillation column 400 may be divided into a middle part area divided by the dividing wall 401, and an upper part area 410 and a lower part area 440, in which the dividing wall is not disposed. Further, the middle part area may be divided into a first middle part area 420 and a second middle part area 430, which are divided by the dividing wall 401, and the second middle part area 430 may be divided into a third middle part area 431 and a fourth middle part area 432, which equally divide the first distillation column 400 into two parts in a longitudinal direction. Specifically, the third middle part area 431 is in contact with the upper part area 410, and the fourth middle part area 432 may be in contact with the lower part area 440. Therefore, the inside of the first distillation column 400 may be divided into the upper part area 410, the lower part area 440, and the middle part area, the middle part area is also divided into the first middle part area 420 and the second middle part area 430, and the second middle part area may be again divided into the third middle part area 431 and the fourth middle part area 432. In the dividing wall-type distillation column of the present application, the first middle part area 420 and the second middle part area 430 in the first distillation column 400 are separated from or isolated from each other by the dividing wall 401. Accordingly, the stream inside of the first middle part area 420 and the stream inside of the second middle part area 430 may be prevented from being mixed with each other. The term "separated from or isolated from" in the present specification means that the stream in each area flows or is present independently from the area separated by the dividing wall 401.

In an example, the dividing wall 401 disposed inside of the first distillation column 400 may be disposed in the middle part area. Specifically, the length of the dividing wall 401, when calculated based on the number of theoretical plates of the first distillation column 400, may be a length corresponding to the number of plates of 40% or more of the total number of theoretical plates, preferably 50% or more, and more preferably 60% or more. The dividing wall 401 of the first distillation column 400 may be disposed inside of the first distillation column 400 at a length in the range, thereby effectively blocking the stream inside of the first middle part area 420 and the stream inside of the second middle part area 430 from being mixed. In addition, when a stream discharged from a middle plate outflow part 433 is introduced into the second lower plate inflow part 221 of the second distillation column 200, it is possible to prevent the low boiling point component in the stream discharged from the middle plate outflow part 433 from being mixed and discharged.

In an example, a raw material inflow part 421 of the first distillation column 400 may be disposed in the first middle part area 420 of the first distillation column 400. Furthermore, a first upper plate outflow part 411 and a first upper plate inflow part 412 may be disposed in the upper part area 410 of the first distillation column 400, and the first upper plate outflow part 411 may be preferably disposed at the column top inside of the upper part area 410 of the first distillation column 400. Further, a first lower plate outflow part 441 and a first lower plate inflow part 442 may be disposed in the lower part area 440 of the first distillation column 400, and the first lower plate outflow part 441 may be preferably disposed at the column bottom inside of the lower part area 440 of the first distillation column 400. Furthermore, the middle plate outflow part 433 and a middle plate inflow part 434 of the first distillation column 400 may be disposed in the second middle part area 430 of the first distillation column 400, and preferably disposed in the fourth middle part area 432 included in the second middle part area 430. At this time, the middle plate outflow part 433 may be disposed in the fourth middle part area 432 which is a part on a relatively low side inside of the second middle part area 430, thereby preventing the low boiling point component from being included in the stream discharged from the middle plate outflow part 433 of the first distillation column 400.

In the distillation apparatus, the middle plate outflow part 433 may be disposed at a part lower than the raw material inflow part 421, and the middle plate inflow part 434 may be disposed at a part lower than the middle plate outflow part 433. As described above, the middle plate inflow part 434 may be disposed at a part lower than the middle plate outflow part 433, and the gas/liquid may be smoothly brought into contact with each other, thereby maintaining the separation performance. In an example, the middle plate outflow part 433 and the middle plate inflow part 434 may be disposed at the same plate. For example, the middle plate outflow part 433 and the middle plate inflow part 434 may be disposed at the same plate inside of the second middle part area 430 of the dividing wall-type distillation column 400, and in this case, the middle plate inflow part 434 may be disposed on a side lower than the middle plate outflow part 433 within the same plate. Accordingly, the middle plate outflow stream ($F_{1-4}$) discharged from the middle plate outflow part 433 of the first distillation column 400 and a second distillation column lower plate outflow stream ($F_{2-1}$) introduced into the middle plate inflow part 434 of the first distillation column 400 may be discharged from and introduced into the same plate of the first distillation column 400. When the middle plate outflow part 433 and the middle plate inflow part 434 are disposed at the same plate, introduction and discharge occur at the same plate, and thus the gas/liquid may be smoothly brought into contact with each other and the hydraulic stream may smoothly occur.

In an example, in order to perform the process of separating three components having a low boiling point, an intermediate boiling point, and a high boiling point from the raw material ($F_{1-1}$) including the three components, respectively, the raw material ($F_{1-1}$) may be introduced into the first middle part area 420 of the first distillation column 400 as illustrated in FIG. 14. In an example, the raw material ($F_{1-1}$) is introduced into the raw material inflow part 421 disposed in the first middle part area 420 of the first distillation column 400, a low boiling point stream having a relatively low boiling point among the components included in the raw material ($F_{1-1}$) is introduced into the upper part area 410, and a high boiling point stream having a relatively high boiling point is introduced into the lower part area 440. Further, the stream introduced into the upper part area 410 is discharged into a first distillation column upper plate outflow stream ($F_{1-2}$) in the first upper plate outflow part 411 and passes through a condenser 402, and a part thereof flows back to the first upper plate inflow part 412 of the first distillation column 400, or is stored as a product. In addition, the stream introduced into the lower part area 440 is discharged into a first distillation column lower plate outflow stream ($F_{1-3}$) in the first lower plate outflow part 441 and passes through a reboiler 403, and a part thereof flows back to the first lower plate inflow part 442 of the first distillation column 400, or is stored as a product. A stream of a component having a relatively high boiling point in the stream introduced into the upper part area 410 and a stream of a component having a relatively low boiling point in the stream introduced into the lower part area 440 are introduced into the second middle part area 430, and may be discharged from the middle plate outflow part 433 of the fourth middle part area (432) and introduced into the second distillation column 200.

In this case, the temperature of the upper part area 410 of the first distillation column 400 may be 80 to 115° C., 85 to 100° C., or 90 to 105° C., the temperature of the lower part area 440 of the first distillation column 400 may be 120 to 160° C., 130 to 155° C., or 135 to 147° C., and the temperature of the second middle part area 430 of the first distillation column 400 may be 100 to 150° C., 110 to 140° C., or 120 to 135° C. Furthermore, the reflux ratio of the first distillation column upper plate outflow stream ($F_{1-2}$) which flows back to the first upper plate outflow part 411 of the first distillation column 400 in the first distillation column upper plate outflow stream ($F_{1-2}$) of the first distillation column 400 may be 1 to 10, and may be preferably 1.2 to 7.0, or 1.5 to 4.5 from the thermodynamic viewpoint. The reflux ratio of the first distillation column lower plate outflow stream ($F_{1-3}$) which flows back to the first lower plate inflow part 442 of the first distillation column 400 in the first distillation column lower plate outflow stream ($F_{1-3}$) of the first distillation column 400 may be 1 to 30, and may be preferably 5 to 25, or 10 to 20 from the thermodynamic viewpoint. Further, the temperature of the upper part 210 of the second distillation column may be 100 to 130° C., 104 to 125° C., or 108 to 120° C., and the temperature of the lower part 220 of the second distillation column may be 120 to 150° C., 120 to 140° C., or 123 to 133° C. In addition, the reflux ratio of a second distillation column upper plate outflow stream ($F_{2-2}$) which flows back to the second upper plate inflow part 212 of the second distillation column 200 in the second distillation column upper plate outflow stream ($F_{2-2}$) of the second distillation column 200 may be 0.01 to 5.0, and may be preferably 0.05 to 1.0, or 0.1 to 2.0 from the thermodynamic viewpoint.

In an example, the distillation apparatus including the first distillation column 400 may include a heater 300 or a heat exchanger, which preheats the raw material ($F_{1-1}$). Furthermore, two or more openings may be formed in one or more of the inflow part and the outflow part of the first distillation column 400, thereby enhancing the separation efficiency of the raw material ($F_{1-1}$). The detailed description on that is the same as that described in the above-described distillation apparatus, and thus, will be omitted.

FIG. 15 is a view exemplarily illustrating a distillation apparatus according to still yet another exemplary embodiment of the present application.

As illustrated in FIG. 15, the distillation apparatus includes a first distillation apparatus and a second distillation apparatus, and a first distillation column 500 included in the first distillation apparatus may be a dividing wall-type distillation column including a dividing wall 501 therein. The first distillation column 500 may have a structure in which the dividing wall 501 is in contact with the column top of the first distillation column 500, and separated from the column bottom thereof. Accordingly, as divided by virtual dotted lines in the drawing, the inside of the first distillation column 500 may be divided into a first area 510 and a third area 530 divided by the dividing wall 501, and a second area 520 in which the dividing wall 501 is not disposed and which is disposed at the lower plate of the first area 510 and the third area 530. The first area 510 may be divided into a first upper part area 511 and a first lower part area 512, which divide the first distillation column 500 into two parts in a longitudinal direction, the first upper part area 511 may not be in contact with the second area 520, and the first lower part area 512 may be in contact with the second area 520. Further, the third area 530 may be divided into a third upper part area 531 and a third lower part area 532, which equally divide the first distillation column 500 into two parts in a longitudinal direction, the third upper part area 531 may not be in contact with the second area 520, and the third lower part area 532 may be in contact with the second area 520. Accordingly, the inside of the first distillation column 500 is divided into the first area 510, the second area 520, and the third area 530, the first area 510 may be divided into the first upper part area 511 and the first lower part area 512, and the third area 530 may be again divided into the third upper part area 531 and the third lower part area 532. For example, the first area 510 and the third area 530 in the first distillation column 500 are separated from or isolated from each other by the dividing wall 501. Accordingly, the stream discharged from first area 510 and the stream discharged from the third area 530 may be prevented from being mixed with each other.

In an example, the length of the dividing wall 501, when calculated based on the number of theoretical plates of the first distillation column 500, may be a length corresponding to the number of plates of 40% or more of the total number of theoretical plates, preferably 50% or more, and more preferably 60% or more. As described above, the dividing wall 501 of the first distillation column 500 may be disposed inside of the first distillation column 500 at a length in the range, thereby effectively blocking the stream inside of the first area 510 and the stream inside of the third area 530 from being mixed. In addition, the dividing wall 501 is in contact with the column top, thereby more effectively preventing the low boiling point component from being discharged while being mixed with a stream discharged from a middle plate outflow part 533 than the case of the distillation column having the dividing wall 401 of FIG. 14 when the stream discharged from the middle plate outflow part 533 is introduced into the second lower plate inflow part 221 of the second distillation column 200.

In an exemplary embodiment, the first area 510 includes a raw material inflow part 513, a first upper plate outflow part 514, and a first upper plate inflow part 515, the second area 520 includes a first lower plate outflow part 521 and a first lower plate inflow part 522, and the third area 530 includes a third upper plate inflow part 536, a third upper plate outflow part 535, the middle plate outflow part 533 and a middle plate inflow part 534. For example, the raw material inflow part 513, the first upper plate outflow part 514, and the first upper plate inflow part 515 are disposed in the first area 510 of the first distillation column 500, the third upper plate inflow part 536, the third upper plate outflow part 535, the middle plate outflow part 533, and the middle plate inflow part 534 are disposed in the third area 530, and the first lower plate outflow part 521 and the first lower plate inflow part 522 may be disposed in the second area 520. Specifically, the raw material inflow part 513 may be disposed in the first lower part area 512 or at a point in which the first upper part area 511 and the first lower part area 512 are in contact with each other. The point in which the first upper part area 511 and the first lower part area 512 are in contact with each other may refer to a point which equally divide the first distillation column 500 into two parts in a longitudinal direction. Furthermore, the first upper plate outflow part 514 and the first upper plate inflow part 515 may be disposed in the first upper part area 511 included in the first area 510 of the first distillation column 500, and the first upper plate outflow part 514 may be preferably disposed at the column top inside of the first upper part area 511 of the first distillation column 500. Further, the first lower plate outflow part 521 and the first lower plate inflow part 522 may be disposed in the second area 520 of the first distillation column 500, and the first lower plate outflow part 521 may be preferably disposed at the column bottom inside of the second area 520 of the first distillation column 500. In addition, the third upper plate inflow part 536, the third upper plate outflow part 535, the middle plate outflow part 533, and the middle plate inflow part 534 may be disposed at the third area 530 of the first distillation column 500. In an example, the third upper plate inflow part 536 and the third upper plate outflow part 535 may be disposed in the third upper part area 531, the third upper plate inflow part 536 is disposed at the uppermost plate of the third area 530, for example, the first plate, and the third upper plate outflow part 535 may be disposed at the column top of the third area 530. Furthermore, the middle plate outflow part 533 and the middle plate inflow part 534 may be disposed in the third lower part area 532. The middle plate outflow part 533 and the middle plate inflow part 534 may be disposed in the third lower part area 532, thereby preventing the low boiling point component from being included in the stream discharged from the middle plate outflow part 533 of the first distillation column 500. In the distillation apparatus, the middle plate outflow part 533 may be disposed at a part lower than the raw material inflow part 513, the middle plate inflow part 534 may be disposed at a part lower than the middle plate outflow part 533, and the description on this is the same as that described above, and thus, will be omitted.

In an example, in order to perform the process of separating three components having a low boiling point, an intermediate boiling point, and a high boiling point from a raw material ($F_{1-1}$) including the three components, respectively, the raw material ($F_{1-1}$) may be introduced into the first area 510 of the first distillation column 500 as illustrated in FIG. 15. In an example, the raw material ($F_{1-1}$) is introduced into the raw material inflow part 513 disposed in the first area 510 of the first distillation column 500, a low boiling point stream having a relatively low boiling point among the components included in the raw material ($F_{1-1}$) is introduced into the first upper part area 511, and a high boiling point stream having a relatively high boiling point passes through the first lower part area 512, and may be introduced into the second area 520. The stream introduced into the first upper part area 511 is discharged into a first area upper plate outflow stream ($F_{1-2}$) in the first upper plate outflow part 514, and passes through a first condenser 502, and a part thereof may be introduced into the first upper plate inflow part 515 of the first area 510. A high boiling point stream having a relatively high boiling point in the stream introduced into the second area 520 is discharged into a first distillation column lower plate outflow stream ($F_{1-3}$) in the first lower plate outflow part 521 and passes through a reboiler 504, and a part thereof may be introduced into the first lower plate inflow part 522 of the second area 520. An intermediate boiling point stream having a relatively low boiling point in the stream introduced into the second area 520 is introduced into the third area 530 and is separated into a component having a relatively low boiling point and a component having a relative high boiling point among the components introduced into the third area 530, and a part thereof may also be re-introduced into the first area 510. A component having a relatively low boiling point among the components introduced into the third area 530 is discharged into a third area upper plate outflow stream ($F_{1-5}$) in the third upper plate outflow part 535 of the third upper part area 531 and passes through a third condenser 503, and a part thereof may be introduced into the third upper plate inflow part 536 of the third area 530. Further, a component having a relatively high boiling point among the components introduced into the third area 530 is discharged from the middle plate outflow part 533 of the third lower part area 532 and introduced into the second distillation column 200, or may be again introduced into the second area 520.

In this case, the temperature of the first upper part area 511 of the first distillation column 500 may be 80 to 115° C., 85 to 100° C., or 90 to 105° C., the temperature of the second area 520 of the first distillation column 500 may be 120 to 160° C., 130 to 155° C., or 135 to 147° C., and the temperature of the third upper part area 531 of the first distillation column 500 may be 85 to 120° C., 90 to 105° C., or 95 to 110° C. In addition, the reflux ratio of the first area upper plate outflow stream ($F_{1-2}$) which flows back to the first upper plate inflow part 515 of the first area 510 in the first area upper plate outflow stream ($F_{1-2}$) discharged from the first area 510 may be 1 to 10, and may be preferably 1.2 to 7.0 or 1.5 to 4.5 from the thermodynamic viewpoint. The reflux ratio of the third area upper plate outflow stream ($F_{1-5}$)

which flows back to the third upper plate inflow part 536 of the third area 530 in the third area upper plate outflow stream ($F_{1-5}$) discharged from the third area 530 may be 0.01 to 3.0, and may be preferably 0.03 to 2.0 or 0.1 to 1.0 from the thermodynamic viewpoint. The reflux ratio of the first distillation column lower plate outflow stream ($F_{1-3}$) which flows back to the first lower plate inflow part 522 of the second area 520 in the first distillation column lower plate outflow stream ($F_{1-3}$) of the second area 520 may be 1 to 30, and may be preferably 5 to 25, or 10 to 20 from the thermodynamic viewpoint. Furthermore, the temperature of the upper part 210 of the second distillation column may be 100 to 130° C., 104 to 125° C., or 108 to 120° C., and the temperature of the lower part 220 of the second distillation column may be 120 to 150° C., 120 to 140° C., or 123 to 133° C. Further, the reflux ratio of a second distillation column upper plate outflow stream ($F_{2-2}$) which flows back to the second upper plate inflow part 212 of the second distillation column 200 in the second distillation column upper plate outflow stream ($F_{2-2}$) of the second distillation column 200 may be 0.01 to 5.0, and may be preferably 0.05 to 1.0, or 0.1 to 2.0 from the thermodynamic viewpoint.

In an example, the distillation apparatus including the first distillation column 500 may include a heater 300 or a heat exchanger, which preheats the raw material ($F_{1-1}$). In addition, two or more openings may be formed in one or more of the inflow part and the outflow part of the first distillation column 500, thereby enhancing the separation efficiency of the raw material ($F_{1-1}$). The detailed description on that is the same as that described in the above-described distillation apparatus, and thus, will be omitted.

The present application also relates to a method for separating a raw material, and for example, the separation method may be performed by the above-described distillation apparatus.

The method for separating a raw material ($F_{1-1}$) of the present application may include: introducing the raw material ($F_{1-1}$); distilling and classifying the raw material ($F_{1-1}$); and separating and discharging the raw material ($F_{1-1}$). Specifically, the method may include: introducing the raw material ($F_{1-1}$) into a raw material inflow part 121 of a first distillation column 100; separating and discharging the raw material ($F_{1-1}$) introduced into the first distillation column 100 into a first upper plate outflow part 111, a middle plate outflow part 122, and a first lower plate outflow part 131 of the first distillation column 100; introducing the stream discharged from the middle plate outflow part 122 into a second lower plate inflow part 221 of a second distillation column 200; and separating the stream introduced into the second distillation column 200 to separate and discharge the stream each at a second upper plate outflow part 211 and a second lower plate outflow part 222 of the second distillation column 200.

[Formula 1]

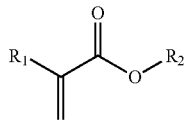

The raw material ($F_{1-1}$) introduced into the first distillation column 100 may include the compound of Formula 1, and may be, for example, butyl acrylate, methyl acrylate, methyl methacrylate, 2-ethylhexyl acrylate, acrylic acid, ethylene glycol, butyl acrylate, methyl alcohol, or isopropyl alcohol, preferably 2-ethylhexyl acrylate. The description on the raw material ($F_{1-1}$) is the same as that described above, and thus, will be omitted.

The separation method may include: separating by the first distillation column 100; and separating by the second distillation column 200 connected to the first distillation column 100. The separating by the first distillation column 100 may include: introducing the raw material ($F_{1-1}$); distilling the raw material ($F_{1-1}$); and separating and discharging the raw material ($F_{1-1}$). In the introducing of the raw material ($F_{1-1}$), the raw material ($F_{1-1}$) may be introduced into the raw material inflow part 121 of the first distillation column 100. In addition, in the distilling of the raw material ($F_{1-1}$), the raw material ($F_{1-1}$) introduced into the first distillation column 100 may be separated each into the first upper plate outflow part 111, the middle plate outflow part 122, and the first lower plate outflow part 131 of the first distillation column 100. Furthermore, in the separating and discharging of the raw material ($F_{1-1}$), the relatively low boiling point stream in the raw material ($F_{1-1}$) may be discharged from the first upper plate outflow part 111 of the first distillation column 100 to a first distillation column upper plate outflow stream ($F_{1-2}$), the relatively high boiling point stream may be discharged from the first lower plate outflow part 131 of the first distillation column 100 to a first distillation column upper plate outflow stream ($F_{1-3}$), and the relatively intermediate boiling point stream may be discharged from the middle plate outflow part 122 of the first distillation column 100 to a middle plate outflow stream ($F_{1-4}$). Further, the separating by the first distillation column 100 includes: allowing a stream discharged from the first upper plate outflow part 111 to pass through a first condenser 101 and introducing a part or all of the first distillation column upper plate outflow stream ($F_{1-2}$) which has passed through the first condenser 101 into a first upper plate inflow part 112, includes: allowing a stream discharged from the first lower plate outflow part 131 to pass through a reboiler 102 and introducing a part or all of the first distillation column lower plate outflow stream ($F_{1-3}$) which has passed through the reboiler 102 into a first lower plate inflow part 132, and may include: introducing a stream discharged from the middle plate outflow part 122 of the first distillation column 100 into the second lower plate inflow part 221 of the second distillation column 200.

The separation method of the present application may include separating by the second distillation column 200 after separating by the first distillation column 100. The separating by the second distillation column 200 may include: introducing the stream discharged from the first distillation column 100, distilling the stream introduced from the first distillation column 100, and separating and discharging the stream. The separating by the second distillation column 200 may include: introducing a stream discharged from the middle plate outflow part 122 of the first distillation column 100 into the second lower plate inflow part 221 of the second distillation column 200. In addition, in the distilling by the second distillation column 200, the stream introduced into the second lower plate inflow part 221 of the second distillation column 200 may be each separated into the second lower plate outflow part 222 and the second upper plate outflow part 211 of the second distillation column 200. Furthermore, the separating and discharging by the second distillation column 200 may include: discharging a relatively high boiling point stream in the stream introduced into the second distillation column 200 from the second lower plate outflow part 222 of the second distillation column 200 into a second distillation column lower plate outflow stream ($F_{2-1}$), and discharging a relatively intermediate boiling point stream from the second upper plate outflow part 211 of the second distillation column 200 into a second distillation column upper plate outflow stream ($F_{2-2}$). Further, the separating and discharging by the second distillation column 200 includes: introducing a part or all of the stream discharged from the second lower plate outflow part 222 into the middle plate inflow part 123 of the first distillation column 100, and may include: allowing the stream discharged from the second upper plate outflow part 211 to pass through a second condenser 201, and introducing a part or all of the stream which has passed through the second condenser 201 into the second upper plate inflow part 212.

In an example, the separating by the first distillation column 100 includes: discharging the stream discharged from the middle plate outflow part 122 of the first distillation column 100 into a plate lower than the stream introduced from the raw material inflow part 121, and may include: introducing the stream introduced into the middle plate inflow part 123 of the first distillation column 100 into a plate lower than the stream discharged from the middle plate outflow part 122. For example, the stream discharged from the middle plate inflow part 123 of the first distillation column 100 may be discharged from a plate upper than the first lower plate outflow part 131 and the first lower plate inflow part 132. In addition, the introducing of the stream discharged from the first distillation column 100 into the second distillation column 200 may include: introducing the stream discharged from the middle plate outflow part 122 of the first distillation column 100 into the column bottom of the second distillation column 200, for example, the second lower plate inflow part 221. Meanwhile, the separating and discharging of the stream introduced into the second distillation column 200 may include: discharging a stream including a lower part product of the second distillation column 200 from the column bottom of the second distillation column 200, for example, the second lower plate outflow part 222, and introducing a part or all of the stream discharged from the second lower plate outflow part 222 of the second distillation column 200 into the middle plate inflow part 123 of the first distillation column 100. In this case, the specific description on the number of theoretical plates of the first distillation column 100, the plate in which the inflow part and the outflow part of the first distillation column 100 are disposed, and the temperature and reflux ratio of each stream is the same as that described in the above-described distillation apparatus, and thus, will be omitted.

The separation method has been described by closely linking each step, but the sequence of the separation method is not limited to that exemplified as described above. Further, since a process step which may be usually performed in the art to which the present application pertains may be additionally included before or after each step, the separation method is not limited only to the steps.

In addition, the separation method of the present application may additionally include: preheating the raw material ($F_{1-1}$) before being introduced into the first distillation column 100. The term "preheating" or "preheat" is used to have the same meaning as the preheating below. Since the preheating is performed before introducing the above-described raw material ($F_{1-1}$) and the raw material ($F_{1-1}$) may be heated before being introduced into the raw material inflow part 121 of the first distillation column 100, it is possible to minimize energy loss generated during the separation process of the raw material ($F_{1-1}$). In the preheating, the raw material ($F_{1-1}$) to be introduced into the first distillation column 100 may be preheated using an external heat source. In the exemplary heating, the raw material ($F_{1-1}$) may be heated using a heater 300. Accordingly, before being introduced into the first distillation column 100, the raw material ($F_{1-1}$) may be heated to reduce the amount of heat consumed to be used in the reboiler 102 in order to heat a part of the stream to flow back to the first lower plate inflow part 132 in the first distillation column lower plate outflow stream ($F_{1-3}$) of the first distillation column 100. The specific contents on the heater 300 are the same as those described above, and thus, will be omitted.

Furthermore, the separation method of the present application may include heat-exchanging the first distillation column upper plate outflow stream ($F_{1-2}$) of the first distillation column 100 with the raw material ($F_{1-1}$) by using a first heat exchanger 301. In this case, the first distillation column upper plate outflow stream ($F_{1-2}$) discharged from the first distillation column 100 supplies heat while passing through the first heat exchanger 301, and may increase the temperature of the raw material ($F_{1-1}$) using the first heat exchanger 301. Further, in an example, the separation method of the present application may include heat-exchanging a second distillation column upper plate outflow stream ($F_{2-2}$) discharged from the second distillation column 200 with the raw material ($F_{1-1}$) by using a second heat exchanger 302. In this case, the second distillation column upper plate outflow stream ($F_{2-2}$) discharged from the second distillation column 200 supplies heat while passing through the second heat exchanger 302, and may increase the temperature of the raw material ($F_{1-1}$) using the second heat exchanger 302. Accordingly, the low-temperature raw material ($F_{1-1}$) introduced into the first distillation column 100 is heated by utilizing waste heat discharged from the separation process of the raw material ($F_{1-1}$), and it is possible to minimize energy loss generated in the separation process. In addition, the temperature of the raw material may be efficiently increased only by heat energy less than the case where sensible heat of the liquid is utilized by using latent heat generated from the high-temperature steam.

Furthermore, the first distillation column upper plate outflow stream ($F_{1-2}$) of the first distillation column 100 supplies the first heat exchanger 301 with heat, and then flows back to the first upper plate inflow part 112 of the first distillation column 100 at a relatively low temperature, and the second distillation column upper plate outflow stream ($F_{2-2}$) of the second distillation column 200 supplies the second heat exchanger 302 with heat, and then flows back to the second upper plate inflow part 212 of the second distillation column 200 at a relatively low temperature. Accordingly, the costs required for a condensing process may be reduced by decreasing the amount of cooling water used in the condensing process using the first condenser 101 and the second condenser 201. Further, it is possible to reduce the amount of heat consumed to be used in the reboiler 102 in order to heat a part or all of the stream to flow back to the first lower plate inflow part 132 in the first distillation column lower plate outflow stream ($F_{1-3}$) of the first distillation column 100. From this, the amount of energy consumed for increasing the temperature of the raw material ($F_{1-1}$) to be introduced into the first distillation column 100 may be reduced, and the size of the distillation column used for the purification may also be minimized, thereby enhancing the economic efficiency of the process. In this case, the detailed description on the temperature and reflux ratio of the raw material ($F_{1-1}$) and each stream is the same as the distillation apparatus described above, and thus, will be omitted.

According to the distillation apparatus of the present application and the separation method using the same, the amount of energy consumed may be reduced, and the size of the distillation column used for purifying the raw material may also be minimized, thereby enhancing the economic efficiency of the process.

Advantageous Effects

According to the distillation apparatus of the present application, it is possible to separate a material to be separated during the separation of a mixture of three or more components, for example, 2-ethylhexyl acrylate with high purity, and to achieve an object of saving energy during the separation and purification process of 2-ethylhexyl acrylate.

BRIEF DESCRIPTION OF DRAWINGS

FIG. 1 is a view exemplarily illustrating a distillation apparatus according to exemplary embodiments of the present application.

FIGS. 2 and 3 are views exemplarily illustrating a distillation apparatus according to an exemplary embodiment of the present application.

FIG. 4 is a view exemplarily illustrating a distillation apparatus according to an exemplary embodiment of the present application.

FIGS. 5 and 6 are views exemplarily illustrating a distillation apparatus according to another exemplary embodiment of the present application.

FIGS. 7 to 13 are views exemplarily illustrating a cross section of the distillation apparatus according to an exemplary embodiment of the present application, which is in parallel with the ground surface.

FIG. 14 is a view exemplarily illustrating a distillation apparatus according to yet another exemplary embodiment of the present application.

FIG. 15 is a view exemplarily illustrating a distillation apparatus according to still yet another exemplary embodiment of the present application.

FIG. 16 is a view exemplarily illustrating a general separation device used in Comparative Example.

BEST MODE

Hereinafter, the present application will be described in more detail with reference to Examples which follow the present application and Comparative Example which does not follow the present application, but the scope of the present application is not limited by the following Examples.

EXAMPLE 1

2-Ethylhexyl acrylate was prepared by using the distillation apparatus of FIG. 1. Specifically, the raw material including 2-ethylhexyl acrylate at 20° C. to 40° C. was introduced into the fifteenth plate of a first distillation column in which the number of theoretical plates was 60.

The operation pressure of the first distillation column upper part was allowed to be about 20 to 30 torr, the operation temperature was allowed to be about 90 to 105° C., the operation pressure of the first distillation column lower part was allowed to be about 80 to 90 torr, and the operation temperature was allowed to be 140 to 147° C. A part of the stream discharged from the first plate of the first distillation column was allowed to pass through a first condenser and flow back to the first distillation column, a part of the stream discharged from the sixtieth plate of the first distillation column was allowed to pass through a reboiler and flow back to the first distillation column, and at this time, the reflux ratio of the first distillation column upper plate outflow stream of the first distillation column was set to be 1.5 to 4.5, and the reflux ratio of the first distillation column lower plate outflow stream was set to be 10 to 20. Further, a stream discharged from the middle plate outflow part disposed at the fifty fifth plate of the first distillation column was introduced into the second lower plate inflow part of the column bottom of the second distillation column, and a stream discharged from the second lower plate outflow part of the column bottom of the second distillation column was introduced into the middle plate inflow part disposed at the fifty fifth plate of the first distillation column and at a lower part of the middle plate outflow part. In this case, the operation pressure of the second distillation column upper part was allowed to be about 20 to 30 torr, the operation temperature was allowed to be about 108 to 120° C., the operation pressure of the second distillation column lower part was allowed to be about 40 to 60 torr, and the operation temperature was allowed to be 120 to 150° C. A part of a stream including 2-ethylhexyl acrylate to be discharged into the upper part of the second distillation column was allowed to pass through a second condenser, and flow back to the second distillation column, and the other part was separated as a product. In this case, the reflux ratio of the second distillation column upper plate outflow stream of the second distillation column was set to be 0.01 to 5.0.

EXAMPLE 2

As illustrated in FIG. 4, purification was performed in the same manner as in Example 1, except that the raw material was warmed to 50 to 100° C. through a heater, and then introduced into the first distillation column.

EXAMPLE 3

As illustrated in FIG. 5, purification was performed in the same manner as in Example 1, except that the first distillation column upper plate outflow stream discharged from the first upper plate outflow part of the first distillation column was introduced into a first heat exchanger, and was heat-exchanged with the raw material to be introduced into the first distillation column before passing through the first condenser. The temperature of the raw material to be introduced into the first distillation column after the heat exchange was adjusted to 50 to 100° C., and the temperature of the first distillation column upper plate outflow stream to be introduced into the first condenser was adjusted to be 50 to 90° C. In addition, in this case, the operation pressure of the first distillation column upper part was allowed to be about 20 to 30 torr, and the temperature of the first distillation column upper plate outflow stream to be introduced into the first heat exchanger was allowed to be about 80 to 115° C., and the operation pressure of the first distillation column lower part was allowed to be about 80 to 90 torr, and the operation temperature was allowed to be 140 to 147° C. At this time, the reflux ratio of the first distillation column upper plate outflow stream of the first distillation column was set to be 1.5 to 4.5, and the reflux ratio of the first distillation column lower plate outflow stream was set to be 10 to 20. Furthermore, the operation pressure of the second distillation column upper part was allowed to be about 20 to 30 torr, the operation temperature was allowed to be about 108 to 120° C., the operation pressure of the second distillation column lower part was allowed to be about 40 to 60 torr, the operation temperature was allowed to be 120 to 150° C., and the reflux ratio of the second distillation column upper plate outflow stream of the second distillation column was set to be 0.1 to 2.0.

EXAMPLE 4

As illustrated in FIG. 6, purification was performed in the same manner as in Example 3, except that the second distillation column upper plate outflow stream discharged from the second upper plate outflow part of the second distillation column was introduced into a second heat exchanger, and was heat-exchanged with the raw material to be introduced into the first distillation column before passing through the second condenser. The temperature of the raw material to be introduced into the first distillation column after the heat exchange was adjusted to 90 to 110° C., and the temperature of the second distillation column upper plate outflow stream to be introduced into the second condenser was adjusted to be 60 to 110° C. In addition, in this case, the operation pressure of the second distillation column upper part was allowed to be about 20 to 30 torr, and the temperature of the second distillation column upper plate outflow stream to be introduced into the second heat exchanger was allowed to be about 100 to 130° C., and the operation pressure of the second distillation column lower part was allowed to be about 40 to 60 torr, and the operation temperature was allowed to be 120 to 150° C. At this time, the reflux ratio of the second distillation column upper plate outflow stream of the second distillation column was set to be 0.01 to 5.0.

EXAMPLE 5

Purification was performed in the same manner as in Example 1, except that a distillation column was used, which was formed such that two openings were formed in the raw material inflow part of the first distillation column, and the two raw material inflow parts were disposed at the fifteenth plate of the first distillation column in which the number of theoretical plates was 60.

EXAMPLE 6

Purification was performed in the same manner as in Example 1, except that a distillation column was used, which was formed such that two openings were formed in each of the raw material inflow part and the first upper plate inflow part of the first distillation column, the two raw material inflow parts were disposed at the fifteenth plate of the first distillation column in which the number of theoretical plates was 60, and the two first upper plate inflow parts were disposed at the first plate of the first distillation column in which the number of theoretical plates was 60.

EXAMPLE 7

Purification was performed in the same manner as in Example 1, except that a distillation column was used, which was formed such that two openings were formed in each of the raw material inflow part and the first lower plate inflow part of the first distillation column, the two raw material inflow parts were disposed at the fifteenth plate of the first distillation column in which the number of theoretical plates was 60, and the two first lower plate inflow parts were disposed at the sixtieth plate of the first distillation column in which the number of theoretical plates was 60.

EXAMPLE 8

Purification was performed in the same manner as in Example 1, except that a distillation column was used, which was formed such that two openings were formed in each of the raw material inflow part, the first lower plate inflow part, and the first upper plate inflow part of the first distillation column, the two raw material inflow parts were disposed at the fifteenth plate of the first distillation column in which the number of theoretical plates was 60, the two first lower plate inflow parts were disposed at the sixtieth plate of the first distillation column in which the number of theoretical plates was 60, and the two first upper plate inflow parts were disposed at the first plate of the first distillation column in which the number of theoretical plates was 60.

EXAMPLE 9

Purification was performed in the same manner as in Example 1, except that a distillation column was used, which was formed such that two openings were formed in each of the raw material inflow part, the middle plate outflow part, and the middle plate inflow part of the first distillation column, the two raw material inflow parts were disposed at the fifteenth plate of the first distillation column in which the number of theoretical plates was 60, the middle plate outflow part was disposed at the fifty fifth plate of the first distillation column in which the number of theoretical plates was 60, and the middle plate inflow part was disposed at a lower part of the middle plate outflow part at the fifty fifth plate of the first distillation column in which the number of theoretical plates was 60, and a distillation column was used, which was formed such that two openings were formed in the second lower plate inflow part of the second distillation column, and the two second lower plate inflow parts were disposed at the column bottom of the second distillation column.

EXAMPLE 10

Purification was performed in the same manner as in Example 1, except that a distillation column was used, which was formed such that two openings were formed in each of the raw material inflow part, the first upper plate inflow part, and the first lower plate inflow part of the first distillation column, the two raw material inflow parts were disposed at the fifteenth plate of the first distillation column in which the number of theoretical plates was 60, the two first upper plate inflow parts were disposed at the first plate of the first distillation column in which the number of theoretical plates was 60, the two first lower plate inflow parts were disposed at the sixtieth plate of the first distillation column in which the number of theoretical plates was 60, and each two of the middle plate outflow part and the middle plate inflow part was disposed at the fifty fifth plate of the first distillation column in which the number of theoretical plates was 60, and a distillation column was used, which was formed such that two openings were formed in the second lower plate inflow part of the second distillation column, and the two second lower plate inflow parts were disposed at the column bottom of the second distillation column.

EXAMPLE 11

Purification was performed in the same manner as in Example 1, except that a dividing wall-type distillation column having a dividing wall was used as the first distillation column as illustrated in FIG. 14. A raw material including 2-ethylhexyl acrylate was introduced into the raw material inflow part disposed in a first middle part area of the first distillation column, and specifically, was introduced into the fifteenth plate of the first distillation column in which the number of theoretical plates was 60. In this case, the operation pressure of the first distillation column upper part area was allowed to be about 20 to 30 torr, the operation temperature was allowed to be about 80 to 115° C., the operation pressure of the first distillation column lower part area was allowed to be about 80 to 90 torr, and the operation temperature was allowed to be 120 to 160° C. A part of the stream discharged from the upper part area of the first distillation column was allowed to pass through the first condenser and flow back to the first distillation column, and a part of the stream discharged from the lower part area of the first distillation column was allowed to pass through the reboiler and flow back to the first distillation column. At this time, the reflux ratio of the first distillation column upper plate outflow stream of the first distillation column was set to be 1 to 10, and the reflux ratio of the first distillation column lower plate outflow stream was set to be 1 to 30. Further, a stream discharged from a fourth middle part area of the first distillation column, specifically, the fifty fifth plate of the first distillation column was introduced into the column bottom of the second distillation column, and a stream discharged from the column bottom of the second distillation column was introduced into the fourth middle part area of the first distillation column, specifically, the fifty fifth plate of the first distillation column. In this case, the operation pressure of the second distillation column upper part was allowed to be about 20 to 30 torr, the operation temperature was allowed to be about 100 to 130° C., the operation pressure of the second distillation column lower part was allowed to be about 40 to 60 torr, and the operation temperature was allowed to be 120 to 150° C. A part of a stream including 2-ethylhexyl acrylate to be discharged into the upper part of the second distillation column was allowed to pass through the second condenser, and flow back to the second distillation column, and the other part was separated as a product. In this case, the reflux ratio of the second distillation column upper plate outflow stream of the second distillation column was set to be 0.01 to 5.0.

EXAMPLE 12

Purification was performed in the same manner as in Example 1, except that a dividing wall-type distillation column having a dividing wall which was in contact with the column top of the distillation column and separated from the column bottom was used as the first distillation column as illustrated in FIG. 15. A raw material including 2-ethylhexyl acrylate was introduced into the raw material inflow part disposed in a first lower part area of the first distillation column, and specifically, was introduced into the fifteenth plate of the first distillation column in which the number of theoretical plates was 60. The operation pressure of a first area of the first distillation column was allowed to be about 20 to 30 torr, the operation temperature was allowed to be about 80 to 115° C., the operation pressure of a second area of the first distillation column was allowed to be about 80 to 90 torr, and the operation temperature was allowed to be 120 to 160° C. A part of the stream discharged from a first upper part area of the first distillation column was allowed to pass through the first condenser and flow back to the first distillation column, and another part thereof was stored as a product. Further, a part of the stream discharged from a third upper part area of the first distillation column was allowed to pass through a third condenser and flow back to the third upper part area, and another part thereof was stored as a product. A part of the stream discharged from the second area of the first distillation column was allowed to pass through the reboiler and flow back to the second area, and another part thereof was stored as a product. At this time, the reflux ratio of the first area upper plate outflow stream of the first distillation column was set to be 1 to 10, the reflux ratio of the third area upper plate outflow stream was set to 0.01 to 3.0, and the reflux ratio of the first distillation column lower plate outflow stream was set to be 1 to 30. In addition, a stream discharged from a third lower part area of the first distillation column, specifically, the middle plate outflow part at the fifty fifth plate of the first distillation column was introduced into the column bottom of the second distillation column, and a stream discharged from the column bottom of the second distillation column was introduced into the third lower part area of the first distillation column, specifically, the middle plate inflow part which was disposed at the fifty fifth plate of the first distillation column, and disposed at the lower part of the middle plate outflow part. In this case, the operation pressure of the second distillation column upper part was allowed to be about 20 to 30 torr, the operation temperature was allowed to be about 100 to 130° C., the operation pressure of the second distillation column lower part was allowed to be about 40 to 60 torr, and the operation temperature was allowed to be 120 to 150° C. A part of a stream including 2-ethylhexyl acrylate to be discharged into the upper part of the second distillation column was allowed to pass through the second condenser, and flow back to the second distillation column, and the other part was separated as a product. In this case, the reflux ratio of the second distillation column upper plate outflow stream of the second distillation column was set to be 0.01 to 5.0.

Comparative Example

As illustrated in FIG. 16, 2-ethylhexyl acrylate was purified by using a distillation apparatus to which two distillation columns were connected. A low boiling point stream and water discharged from the column top area of the first distillation column passed through a condenser, a part thereof was allowed to flow back to the first distillation column, and the other part thereof was produced as a product, the stream discharged from the column bottom area of the first distillation column was again allowed to flow back to the column bottom area of the first distillation column by using a reboiler, and the other part thereof was introduced into the second distillation column. The intermediate boiling point stream discharged from the upper part of the second distillation column was condensed by using a condenser, a part thereof was again allowed to flow back to the column top area of the second distillation column, and the other part thereof was separated as a product, and for the high boiling point stream discharged from the lower part of the second distillation column, a part thereof was again allowed to flow back to the column bottom area of the second distillation column by using a reboiler. In this case, the reflux ratio of the column top stream of the second distillation column was set to be 0.2 to 1.0.

2-Ethylhexyl acrylate was purified according to the Examples and Comparative Example, and then the purity of 2-ethylhexyl acrylate, the content of the low boiling point material in the product, and the amount of energy consumed were measured, and are shown in the following Table 1.

TABLE 1

|  | Comparative Example | Example 1 | Example 2 | Example 3 | Example 4 | Example 11 | Example 12 |
| --- | --- | --- | --- | --- | --- | --- | --- |
| Product purity (wt %) | 99.95 | 99.95 | 99.95 | 99.95 | 99.95 | 99.96 | 99.96 |
| Content of low boiling point material in product | 10 ppm | 10 ppm | 10 ppm | 10 ppm | 10 ppm | 3 ppb | 1 ppb |
| Amount of energy consumed (Gcal/hr) | 1.2 | 0.91 | 0.91 | 0.84 | 0.82 | 0.91 | 0.91 |
| Energy reduction ratio (%) | — | 24 | 24 | 30 | 32 | 24 | 24 |

As shown in Table 1, when 2-ethylhexyl acrylate was purified according to Examples 1 to 4, 11 and 12, 2-ethylhexyl acrylate could be obtained with higher purity than the case where purification was performed according to Comparative Example.

Furthermore, the total amount of energy introduced during the purification process according to Examples 1 to 4, 11 and 12 was 0.91 Gcal/hr, 0.91 Gcal/hr, 0.84 Gcal/hr, 0.82 Gcal/hr, 0.91 Gcal/hr, and 0.91 Gcal/hr, respectively, and it could be confirmed that the total amount of energy consumed was significantly reduced as compared to the total amount of energy introduced during the purification process according to Comparative Example. That is, when 2-ethylhexyl acrylate is separated by the distillation apparatus according to the Examples of the present application, an energy saving effect by up to 32% is shown.

The raw material was separated according to Examples and Comparative Example, and then the degree that channeling occurs during the separation process is shown the following Table 2.

two or more of the inflow part and the outflow part of the present application, the separation efficiency of the raw material may be enhanced as compared to the distillation apparatus according to the Comparative Example.

EXPLANATION OF REFERENCE NUMERALS AND SYMBOLS $F_{1-1}$: Raw material
$F_{1-2}$: First distillation column upper plate outflow stream, First area upper plate outflow stream
$F_{1-3}$: First distillation column lower plate outflow stream
$F_{1-4}$: Middle plate outflow stream
$F_{1-5}$: Second area upper plate outflow stream
$F_{2-1}$: Second distillation column lower plate outflow stream
$F_{2-2}$: Second distillation column upper plate outflow stream
$A_{1-1}, A_{1-2}, A_{1-3}, A_{1-4}$: Small area
100, 400, 500: First distillation column
101, 402, 502: First condenser
102, 403, 504: Reboiler
100: First distillation column upper part
111, 411, 514: First upper plate outflow part
112, 412, 515: First upper plate inflow part

TABLE 2

|  | Comparative Example | Example 1 | Example 5 | Example 6 | Example 7 | Example 8 | Example 9 | Example 10 |
| --- | --- | --- | --- | --- | --- | --- | --- | --- |
| Degree of occurrence of channeling | ○ | ○ | x | x | x | x | x | x |

* x: Channeling not occurred
* o: Channeling occurred

As shown in Table 2, when the raw material was separated according to the Comparative Example by using a general dividing wall-type distillation column and when the raw material was separated according to Example 1 by using a distillation column in which one opening was formed in the raw material inflow part and the reflux inflow part, channeling occurred, but it could be confirmed that in Examples 5 to 10 in which two or more openings were formed in one or more of the raw material inflow part and the reflux inflow part, channeling did not occur during the separation process of the raw material as compared to Comparative Example and Example 1. Therefore, when the raw material is purified by the dividing wall-type distillation column which forms 120: First distillation column middle part
121, 421, 513: Raw material inflow part
122, 433, 533: Middle plate outflow part
123, 434, 534: Middle plate inflow part
130: First distillation column lower part
131, 441, 521: First lower plate outflow part
132, 442, 522: First lower plate inflow part
200: Second distillation column
210: Second distillation column upper part
220: Second distillation column lower part
211: Second upper plate outflow part
212: Second upper plate inflow part
221: Second lower plate inflow part 222: Second lower plate outflow part
201: Second condenser
300: Heater
301: First heat exchanger
302: Second heat exchanger
410: Upper part area
420: First middle part area
440: Lower part area
430: Second middle part area
431: Third middle part area
432: Fourth middle part area
401, 501: Dividing wall
503: Third condenser
510: First area
511: First upper part area
512: First lower part area
520: Second area
530: Third area
531: Third upper part area
532: Third lower part area
535: Third upper plate outflow part
536: Third upper plate inflow part

The invention claimed is:

1. A distillation apparatus comprising:
a first distillation apparatus comprising a first distillation column, a first condenser and a reboiler each connected to the first distillation column; and
a second distillation apparatus comprising a second distillation column and a second condenser connected to the second distillation column,
wherein the first distillation column comprises a raw material inflow part, a first upper plate inflow part, a first upper plate outflow part, a middle plate inflow part, a middle plate outflow part, a first lower plate inflow part, and a first lower plate outflow part, and the second distillation column comprises a second lower plate inflow part, a second lower plate outflow part, a second upper plate inflow part, and a second upper plate outflow part,
a raw material is introduced into the raw material inflow part of the first distillation column, and the introduced raw material is discharged while being separated into a first distillation column upper plate outflow stream discharged from the first upper plate outflow part of the first distillation column, a middle plate outflow stream discharged from the middle plate outflow part, and a first distillation column lower plate outflow stream discharged from the first lower plate outflow part,
the first distillation column upper plate outflow stream discharged from the first upper plate outflow part passes through the first condenser, and a part or all of the first distillation column upper plate outflow stream which has passed through the first condenser is introduced into the first upper plate inflow part to flow back to the first distillation column,
the first distillation column lower plate outflow stream discharged from the first lower plate outflow part passes through a reboiler, and a part or all of the first distillation column lower plate outflow stream which has passed through the reboiler is introduced into the first lower plate inflow part to flow back to the first distillation column,
the middle plate outflow stream discharged from the middle plate outflow part is introduced into the second lower plate inflow part of the second distillation column, and a part or all of a second distillation column lower plate outflow stream discharged from the second lower plate outflow part is introduced into the middle plate inflow part of the first distillation column, and
a second distillation column upper plate outflow stream discharged from the second upper plate outflow part of the second distillation column part passes through the second condenser, and a part or all of the second distillation column upper plate outflow stream which has passed through the second condenser is introduced into the second upper plate inflow part to flow back to the second distillation column;
wherein the middle plate outflow part is formed of two or more openings positioned to be separated from each other at equal intervals in a horizontal cross section of the first distillation column, and
wherein each of the two or more openings of the middle plate outflow part is arranged to face two or more directions.

2. The distillation apparatus of claim 1, wherein the raw material comprises a compound of the following Formula 1:

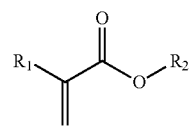

[Formula 1]

in Formula 1,
$R_1$ represents hydrogen, or an alkyl group having 1 to 10 carbon atoms, and
$R_2$ represents a linear or branched alkyl group having 1 to 24 carbon atoms.

3. The distillation apparatus of claim 1, wherein the middle plate outflow part is disposed at a part lower than the raw material inflow part.

4. The distillation apparatus of claim 1, wherein the middle plate inflow part is disposed at a part lower than the middle plate outflow part.

5. The distillation apparatus of claim 4, wherein the middle plate inflow part and the middle plate outflow part are disposed at the same plate.

6. The distillation apparatus of claim 1, wherein the second lower plate inflow part and the second lower plate outflow part are disposed at a column bottom of the second distillation column.

7. The distillation apparatus of claim 1, further comprising a heater which preheats the raw material before being introduced.

8. The distillation apparatus of claim 1, further comprising a first heat exchanger which is disposed at a front plate of the first condenser and heat-exchanges the first distillation column upper plate outflow stream and the raw material.

9. The distillation apparatus of claim 1, further comprising a second heat exchanger which is disposed at a front plate of the second condenser and heat-exchanges the second distillation column upper plate outflow stream and the raw material.

10. The distillation apparatus of claim 1, wherein one or more of the raw material inflow part, the first upper plate inflow part, the middle plate inflow part, the first lower plate inflow part, the second lower plate inflow part, and the second upper plate inflow part is formed of two or more openings disposed to be separated from each other.

11. The distillation apparatus of claim 10, wherein one or more of the second lower plate inflow part, and the second upper plate inflow part is formed of two or more openings disposed to be separated from each other, and the two or more openings are each disposed in two or more small areas which equally divide a horizontal cross section of the second distillation column.

12. The distillation apparatus of claim 1, wherein the first distillation column is a dividing wall distillation column comprising a dividing wall therein.

13. The distillation apparatus of claim 12, wherein the first distillation column comprises an upper part area, a lower part area, and a middle part area in which a dividing wall is disposed, between the upper part area and the lower part area, and the middle part area comprises a first middle part area and a second middle part area each divided by the dividing wall, and
   the raw material inflow part is disposed in the first middle part area, the first upper plate inflow part and the first upper plate outflow part are disposed in the upper part area, the middle plate inflow part and the middle plate outflow part are disposed in the second middle part area, and the first lower plate inflow part and the first lower plate outflow part are disposed in the lower part area.

14. The distillation apparatus of claim 12, further comprising a third upper plate inflow part, a third upper plate outflow part, and a third condenser,
   wherein the dividing wall is in contact with a column top of the first distillation column and separated from a column bottom,
   the first distillation column is divided into a first area and a third area each divided by the dividing wall, and a second area disposed at a side lower than the first area and the third area and in which the dividing wall is not disposed,
   the raw material inflow part, the first upper plate inflow part, and the first upper plate outflow part are disposed in the first area, the first lower plate inflow part and the first lower plate outflow part are disposed in the second area, and the third upper plate inflow part, the third upper plate outflow part, the middle plate inflow part, and the middle plate outflow part are disposed in the third area,
   the raw material is introduced into the raw material inflow part of the first area, and the introduced raw material is discharged into a first area upper plate outflow stream discharged from the first upper plate outflow part of the first area; a first distillation column lower plate outflow stream discharged from the first lower plate outflow part of the second area; the middle plate outflow stream discharged from the middle plate outflow part of the third area; and a third area upper plate outflow stream discharged from the third upper plate outflow part of the third area,
   the first area upper plate outflow stream discharged from the first upper plate outflow part passes through the first condenser, and a part or all of the first area upper plate outflow stream which has passed through the first condenser is introduced into the first upper plate inflow part to flow back to the first area, and
   the third area upper plate outflow stream discharged from the third upper plate outflow part passes through the third condenser, and a part or all of the third area upper plate outflow stream which has passed through the third condenser is introduced into the third upper plate inflow part to flow back to the third area.

15. The distillation apparatus of claim 14, wherein the first area is divided into a first upper part area and a first lower part area, which equally divide the first distillation column into two parts in a longitudinal direction, the first upper part area is not in contact with the second area, the first lower part area is in contact with the second area, the raw material inflow part is disposed in the first lower part area or at a point in which the first upper part area is in contact with the first lower part area, and the first upper plate inflow part and the first upper plate outflow part are disposed in the first upper part area.

16. A distillation apparatus comprising:
   a first distillation apparatus comprising a first distillation column, a first condenser and a reboiler each connected to the first distillation column; and
   a second distillation apparatus comprising a second distillation column and a second condenser connected to the second distillation column,
   wherein the first distillation column comprises a raw material inflow part, a first upper plate inflow part, a first upper plate outflow part, a middle plate inflow part, a middle plate outflow part, a first lower plate inflow part, and a first lower plate outflow part, and the second distillation column comprises a second lower plate inflow part, a second lower plate outflow part, a second upper plate inflow part, and a second upper plate outflow part,
   a raw material is introduced into the raw material inflow part of the first distillation column, and the introduced raw material is discharged while being separated into a first distillation column upper plate outflow stream discharged from the first upper plate outflow part of the first distillation column, a middle plate outflow stream discharged from the middle plate outflow part, and a first distillation column lower plate outflow stream discharged from the first lower plate outflow part,
   the first distillation column upper plate outflow stream discharged from the first upper plate outflow part passes through the first condenser, and a part or all of the first distillation column upper plate outflow stream which has passed through the first condenser is introduced into the first upper plate inflow part to flow back to the first distillation column,
   the first distillation column lower plate outflow stream discharged from the first lower plate outflow part passes through a reboiler, and a part or all of the first distillation column lower plate outflow stream which has passed through the reboiler is introduced into the first lower plate inflow part to flow back to the first distillation column,
   the middle plate outflow stream discharged from the middle plate outflow part is introduced into the second lower plate inflow part of the second distillation column, and a part or all of a second distillation column lower plate outflow stream discharged from the second lower plate outflow part is introduced into the middle plate inflow part of the first distillation column, and
   a second distillation column upper plate outflow stream discharged from the second upper plate outflow part of the second distillation column part passes through the second condenser, and a part or all of the second distillation column upper plate outflow stream which has passed through the second condenser is introduced into the second upper plate inflow part to flow back to the second distillation column;
   wherein one or more of the middle plate outflow part and the second lower plate outflow part is formed of three or more openings positioned to be separated from each other at equal intervals in a horizontal cross section of the first distillation column or the second distillation column, and wherein each of the three or more openings of the middle plate outflow part and the second lower plate outflow part is arranged to face three or more directions.

* * * * *